(12) United States Patent
Nudelman et al.

(10) Patent No.: US 8,916,610 B2
(45) Date of Patent: Dec. 23, 2014

(54) ACID ADDITION SALT OF A NORTRIPTYLINE-GABA CONJUGATE AND A PROCESS OF PREPARING SAME

(75) Inventors: Abraham Nudelman, Rechovot (IL); Ada Rephaeli, Herzlia (IL); Irit Gil-Ad, Herzlia (IL); Abraham Weizman, Tel-Aviv (IL); Mazal Shaul, Azur (IL); Efrat Halbfinger, RaAnana (IL)

(73) Assignees: Ramot at Tel-Aviv University Ltd., Tel-Aviv (IL); Bar-Ilan University, Ramat-Gan (IL)

( * ) Notice: Subject to any disclaimer, the term of this patent is extended or adjusted under 35 U.S.C. 154(b) by 0 days.

(21) Appl. No.: 13/825,369

(22) PCT Filed: Sep. 22, 2011

(86) PCT No.: PCT/IL2011/000752
§ 371 (c)(1),
(2), (4) Date: Mar. 21, 2013

(87) PCT Pub. No.: WO2012/038963
PCT Pub. Date: Mar. 29, 2012

(65) Prior Publication Data
US 2013/0184347 A1 Jul. 18, 2013

Related U.S. Application Data

(60) Provisional application No. 61/385,164, filed on Sep. 22, 2010.

(51) Int. Cl.
| | | |
|---|---|---|
| *A01N 37/30* | (2006.01) |
| *A61K 31/205* | (2006.01) |
| *C07C 57/02* | (2006.01) |
| *C07C 57/18* | (2006.01) |
| *C07C 231/00* | (2006.01) |
| *C07C 237/06* | (2006.01) |
| *C07C 57/15* | (2006.01) |
| *C07C 231/12* | (2006.01) |
| *C07C 231/02* | (2006.01) |
| *C07C 51/41* | (2006.01) |

(52) U.S. Cl.
CPC .............. *C07C 57/15* (2013.01); *C07C 237/06* (2013.01); *C07B 2200/13* (2013.01); *C07C 231/12* (2013.01); *C07C 2103/32* (2013.01); *C07C 231/02* (2013.01); *C07C 51/412* (2013.01)
USPC ............................ 514/554; 562/595; 564/138

(58) Field of Classification Search
None
See application file for complete search history.

(56) References Cited

U.S. PATENT DOCUMENTS

| | | |
|---|---|---|
| 2,914,528 A | 11/1959 | Craig |
| 2,944,053 A | 7/1960 | Edgerton |
| 2,969,358 A | 1/1961 | Cusic |
| 3,227,708 A | 1/1966 | Yale et al. |
| 3,956,493 A | 5/1976 | Yale |
| 3,966,930 A | 6/1976 | Buus et al. |
| 3,978,216 A | 8/1976 | Fuxe |
| 4,153,694 A | 5/1979 | Buus et al. |
| 4,629,691 A | 12/1986 | Collins et al. |
| 4,818,936 A | 4/1989 | Kemlo |
| 5,051,448 A | 9/1991 | Shashoua |
| 5,104,858 A | 4/1992 | Hait et al. |
| 5,145,684 A | 9/1992 | Liversidge et al. |
| 5,420,105 A | 5/1995 | Gustavson et al. |
| 5,525,727 A | 6/1996 | Bodor et al. |
| 5,828,405 A | 10/1998 | Vanier et al. |
| 5,966,673 A | 10/1999 | Shannon |
| 5,983,238 A | 11/1999 | Becker et al. |
| 5,994,392 A | 11/1999 | Shashoua et al. |
| 6,020,954 A | 2/2000 | Aggarwal |
| 6,121,325 A | 9/2000 | Chen et al. |
| 6,197,764 B1 | 3/2001 | Bradley et al. |
| 6,239,867 B1 | 5/2001 | Aggarwal |
| 6,294,562 B1 | 9/2001 | Stilz et al. |
| 6,304,853 B1 | 10/2001 | Malnekoff |
| 6,381,510 B1 | 4/2002 | Amidhozour et al. |
| 6,569,853 B1 | 5/2003 | Borisy et al. |
| 7,544,681 B2 | 6/2009 | Nudelman et al. |
| 7,598,239 B2 | 10/2009 | Nudelman et al. |
| 7,619,006 B2 | 11/2009 | Nudelman et al. |
| 7,939,525 B2 | 5/2011 | Nudelman et al. |
| 8,168,628 B2 | 5/2012 | Nudelman et al. |
| 8,207,369 B2 | 6/2012 | Stein et al. |
| 2001/0024532 A1 | 9/2001 | Malnekoff |

(Continued)

FOREIGN PATENT DOCUMENTS

| | | |
|---|---|---|
| CA | 2461663 | 4/2003 |
| CN | 1596141 | 3/2005 |

(Continued)

OTHER PUBLICATIONS

Haynes et al. (Journal of Pharmaceutical Sciences, 2005, 94, 2111-2120).*

(Continued)

*Primary Examiner* — Dennis Heyer
*Assistant Examiner* — Daniel M Podgorski

(57) ABSTRACT

An acid addition salt of a nortriptyline-GABA conjugate, a novel crystalline form of a fumaric acid addition salt of a nortriptyline-GABA conjugate, and processes of preparing the forgoing are disclosed. Uses of the above-indicated forms of a nortriptyline-GABA conjugate in the treatment of CNS disorders, and in the treatment of pain in particular, are also disclosed. Further disclosed in a large-scale process of preparing a nortriptyline-GABA conjugate.

23 Claims, 5 Drawing Sheets

(56) References Cited

U.S. PATENT DOCUMENTS

| | | |
|---|---|---|
| 2002/0010208 A1 | 1/2002 | Shashoua et al. |
| 2002/0021439 A1 | 2/2002 | Priestley et al. |
| 2002/0052170 A1 | 5/2002 | Holloway |
| 2003/0065586 A1 | 4/2003 | Shaftel et al. |
| 2003/0115079 A1 | 6/2003 | Rapaport |
| 2004/0068417 A1 | 4/2004 | Sevdermish |
| 2004/0092504 A1 | 5/2004 | Benja-Athon |
| 2004/0103447 A1 | 5/2004 | Nawa et al. |
| 2004/0242570 A1 | 12/2004 | Nudelman et al. |
| 2005/0149369 A1 | 7/2005 | Sevdermish |
| 2006/0046967 A1 | 3/2006 | Satyam |
| 2006/0058219 A1 | 3/2006 | Miller |
| 2006/0142181 A1 | 6/2006 | Miller |
| 2007/0099977 A1 | 5/2007 | Nudelman et al. |
| 2007/0197514 A1 | 8/2007 | Nudelman et al. |
| 2007/0219181 A1 | 9/2007 | Kimura et al. |
| 2008/0108606 A1 | 5/2008 | Nudelman et al. |
| 2009/0215809 A1 | 8/2009 | Yao et al. |
| 2009/0298814 A1 | 12/2009 | Nudelman et al. |
| 2009/0304584 A1 | 12/2009 | Nudelman et al. |
| 2010/0063034 A1 | 3/2010 | Nudelman et al. |
| 2010/0120755 A1 | 5/2010 | Nudelman et al. |
| 2010/0204469 A1 | 8/2010 | Nudelman et al. |
| 2011/0312948 A1 | 12/2011 | Nudelman et al. |
| 2012/0277310 A1 | 11/2012 | Stein et al. |
| 2012/0309748 A1 | 12/2012 | Nudelman et al. |
| 2013/0059910 A1 | 3/2013 | Nudelman et al. |
| 2013/0150352 A1 | 6/2013 | Nudelman et al. |

FOREIGN PATENT DOCUMENTS

| | | |
|---|---|---|
| CN | 1997400 | 7/2007 |
| CN | 101247837 | 8/2008 |
| EP | 0361485 | 4/1990 |
| EP | 1429844 | 6/2004 |
| EP | 2272537 | 1/2011 |
| EP | 2275143 | 1/2011 |
| ES | 8707175 | 10/1987 |
| GB | 829246 | 3/1960 |
| GB | 1460713 | 5/1978 |
| GB | 1514312 | 6/1978 |
| GB | 2159636 | 12/1985 |
| GB | 2188630 | 10/1987 |
| GB | 2358541 | 7/2001 |
| IL | 161083 | 9/2002 |
| IL | 199877 | 9/2002 |
| JP | 50-025574 | 3/1975 |
| JP | 53-050185 | 5/1978 |
| JP | 62-501991 | 8/1987 |
| JP | 62-240660 | 10/1987 |
| JP | 02-128564 | 5/1990 |
| JP | 02-188527 | 7/1990 |
| JP | 03-017076 | 2/1991 |
| JP | 06-072868 | 3/1994 |
| JP | 10-059948 | 3/1998 |
| JP | 11-506723 | 6/1999 |
| JP | 2000-020681 | 1/2000 |
| JP | 2001-501965 | 2/2001 |
| JP | 2001-201454 | 7/2001 |
| JP | 2001-519754 | 10/2001 |
| JP | 2003-515564 | 5/2003 |
| JP | 2005-503423 | 2/2005 |
| JP | 2005-097120 | 4/2005 |
| JP | 2005-517669 | 6/2005 |
| JP | 4521187 | 8/2010 |
| WO | WO 86/04991 | 8/1986 |
| WO | WO 93/12496 | 6/1993 |
| WO | WO 96/40687 | 12/1996 |
| WO | WO 97/02819 | 1/1997 |
| WO | WO 97/44063 | 11/1997 |
| WO | WO 98/17678 | 4/1998 |
| WO | WO 98/52898 | 11/1998 |
| WO | WO 99/26661 | 6/1999 |
| WO | WO 01/39779 | 6/2001 |
| WO | WO 01/76576 | 10/2001 |
| WO | WO 01/91011 | 11/2001 |
| WO | WO 02/28881 | 4/2002 |
| WO | WO 02/43652 | 6/2002 |
| WO | WO 03/026563 | 4/2003 |
| WO | WO 03/055424 | 7/2003 |
| WO | WO 03/061656 | 7/2003 |
| WO | WO 03/062942 | 7/2003 |
| WO | WO 2005/032474 | 4/2005 |
| WO | WO 2005/092392 | 10/2005 |
| WO | WO 2006/027711 | 3/2006 |
| WO | WO 2006/058219 | 6/2006 |
| WO | WO 2006/131923 | 12/2006 |
| WO | WO 2007/050318 | 5/2007 |
| WO | WO 2007/139818 | 12/2007 |
| WO | WO 2008/010222 | 1/2008 |
| WO | WO 2008/010223 | 1/2008 |
| WO | WO 2008010223 A2 * | 1/2008 |
| WO | WO 2009/101616 | 8/2009 |
| WO | WO 2011/104637 | 9/2011 |
| WO | WO 2012/038963 | 3/2012 |

OTHER PUBLICATIONS

Haynes et al. (Journal of Pharmaceutical Sciences 2005, 94, 2111-2120).*

Mullin (Crystallization, 2001, Reed Educational and Professional Publishing Ltd, Preface to First Edition).*

Morissette et al. (High-throughput crystallization: polymorphs, salts, co-crystals and solvates of pharmaceutical solids, 2003, Advanced Drug Delivery Reviews, 56, 275-300).*

International Preliminary Report on Patentability Dated Apr. 4, 2013 From the International Bureau of WIPO Re. Application No. PCT/IL2011/000752.

Restriction Official Action Dated May 22, 2013 From the US Patent and Trademark Office Re. U.S. Appl. No. 12/963,959.

Notice of Allowance Dated May 22, 2013 From the US Patent and Trademark Office Re. U.S. Appl. No. 13/531,673.

Examination Report Dated Apr. 17, 2013 From the Instituto Mexicano de la Propiedad Industrial Re. Application No. MX/a/2012/006566 and Its Summary in English.

Official Action Dated Jun. 25, 2013 From the US Patent and Trademark Office Re. U.S. Appl. No. 13/586,913.

Requisition by the Examiner Dated Jun. 27, 2013 From the Canadian Intellectual Property Office Re. Application No. 2,659,521.

Supplementary European Search Report and the European Search Opinion Dated Jun. 25, 2013 From the European Patent Office Re. Application No. 11746937.9.

Translation of Office Action Dated Apr. 25, 2013 From the State Intellectual Property Office of the People's Republic of China Re. Application No. 201080062943.7.

Translation of Search Report Dated Apr. 25, 2013 From the State Intellectual Property Office of the People's Republic of China Re. Application No. 201080062943.7.

Doerwald "Side Reactions in Organic Synthesis", A Guide to Succesful Synthesis Desig, Wiley-VCH Verlag, 4 P., 2005.

Ihara et al. "Noncovalent Binding of Small Ubiquitin-Related Modifier (SUMO) Protease to SUMO Is Necessary for Enzymatic Activities and Cell Growth", The Journal of Biological Chemistry, 282(22): 16465-16475, Jun. 1, 2007.

Nudelmann et al. "A Mutual Prodrug Ester of GABA and Perphenazine Exhibits Antischizophrenic Efficacy with Diminished Extrapyramidical Effects", Journal of Medical Chemistry 51(9) XP002698200, p. 2858-2862, 2008. Scheme 1, Compound (3) with HX Being CH3S03H.

Official Action Dated Jul. 12, 2013 From the US Patent and Trademark Office Re. U.S. Appl. No. 12/963,959.

Requisition by the Examiner Dated Jul. 4, 2013 From the Canadian Intellectual Property Office Re. Application No. 2,610,838.

Drugs "BioLineRx Successfully Completes Phase 1 Clinical Trials of BL-1020, First in Class GABA-Enhanced Antipsychotic for the Treatment of Schizophrenia", Drugs.com, Drug Information Online, 4 P., Feb. 13, 2007.

(56) References Cited

OTHER PUBLICATIONS

Geffen et al. "BL-1020: A Novel Antipsychotic Drug With GABAergic Activity and Low Catalepsy, Is Efficacious in a Rat Model of Schizophrenia", European Neuropsychopharmacology, 19: 1-3, 2009.
Schultz et al. "Schizophrenia: A Review", American Family Physician, 75(12): 1821-1829, Jun. 15, 2007.
Response to Rule 312 Communication Dated Aug. 13. 2013 From the US Patent and Trademark Office Re. U.S. Appl. No. 13/531,673.
Examination Report Dated Sep. 5, 2013 From the Instituto Mexicano de la Propiedad Industrial Re. Application No. MX/a/2012/009821 and Its Translation Into English.
Translation of Decision on Rejection Dated Mar. 28, 2013 From the State Intellectual Property Office of the People's Republic of China Re. Application No. 200810190781.X.
Translation of Notice of Reason for Rejection Dated May 10, 2013 From the Japanese Patent Office Re. Application No. 2010-008725.
Translation of Notification of Office Action Dated May 31, 2013 From the State Intellectual Property Office of the People's Republic of China Re. Application No. 201180020723.2.
Translation of Search Report Dated May 31, 2013 From the State Intellectual Property Office of the People's Republic of China Re. Application No. 201180020723.2.
Communication Pursuant to Rules 70(2) and 70a(2) EPC Dated Jul. 12, 2013 From the European Patent Office Re. Application No. 11746937.9.
Examiner-Initiated Interview Summary and Notice of Abandonment Dated Jul. 8, 2013 From the US Patent and Trademark Office Re. U.S. Appl. No. 11/921,578.
Office Action Dated Jun. 23, 2013 From the Israel Patent Office Re. Application No. 202291 and Its Translation Into English.
Restriction Official Action Dated Mar. 19, 2013 From the US Patent and Trademark Office Re. U.S. Appl. No. 13/586,913.
Advisory Action Before the Filing of An Appeal Brief Dated Jan. 10, 2012 From the US Patent and Trademark Office Re. U.S. Appl. No. 12/656,048.
Advisory Action Before the Filing of an Appeal Brief Dated Aug. 17, 2012 From the US Patent and Trademark Office Re. U.S. Appl. No. 11/921,578.
Advisory Action Before the Filing of an Appeal Brief Dated Oct. 25, 2011 From the US Patent and Trademark Office Re. U.S. Appl. No. 12/764,124.
Applicant-Initiated Interview Summary Dated Apr. 19, 2012 From the US Patent and Trademark Office Re. U.S. Appl. No. 12/656,048.
Communication Pursuant to Article 94(3) Dated Apr. 2, 2008 From the European Patent Office Re.: Application No. 06756205.8.
Communication Pursuant to Article 94(3) EPC Dated Apr. 11, 2011 From the European Patent Office Re. Application No. 09711260.1.
Communication Pursuant to Article 94(3) EPC Dated Dec. 16, 2010 From the European Patent Office Re. Application No. 02772790.8.
Communication Pursuant to Article 94(3) EPC Dated Nov. 24, 2010 From the European Patent Office Re. Application No. 07789958.1.
Communication Pursuant to Article 94(3) EPC Dated Jan. 26, 2012 From the European Patent Office Re. Application No. 10182948.9.
Communication Pursuant to Article 96(2) EPC Dated Nov. 24, 2006 From the European Patent Office Re.: Application No. 02772790.8.
Communication Pursuant to Rules 70(2) and 70a(2) EPC Dated Jan. 31, 2011 From the European Patent Office Re. Application No. 10182948.9.
Communication Relating to the Results of the Partial International Search Dated May 10, 2007 From the International Searching Authority Re.: Application No. PCT/IL2006/000666.
Communication Relating to the Results of the Partial International Search Dated Jun. 13, 2006 From the International Searching Authority Re.: Application No. PCT/IL2005/000341.
Communication Relating to the Results of the Partial International Search Dated Nov. 20, 2007 From the International Searching Authority Re.: Application No. PCT/IL2007/000902.
Communication Relating to the Results of the Partial International Search Dated Nov. 27, 2007 From the International Searching Authority Re.: Application No. PCT/IL2007/000903.
Communication Under Rule 112 EPC Dated Oct. 2, 2007 From the European Patent Office Re.: Application No. 05718914.4.
Communication Under Rule 71(3) EPC Dated May 7, 2012 From the European Patent Office Re.: Application No. 06756205.8.
Communication Under Rule 71(3) EPC Dated Feb. 20, 2012 From the European Patent Office Re. Application No. 09711260.1.
Communication Under Rule 71(3) EPC Dated Sep. 21, 2011 From the European Patent Office Re. Application No. 02772790.8.
Communication Under Rule 71(3) EPC Dated Nov. 28, 2011 From the European Patent Office Re. Application No. 07789958.1.
Communication Under Rule 71(3) EPC Dated Jul. 30, 2012 From the European Patent Office Re. Application No. 10182948.9.
Decision to Grant a European Patent Pursuant to Article 97(1) EPC Dated Aug. 2, 2012 From the European Patent Office Re. Application No. 07789958.1.
English Summary of Examination Report Dated Sep. 4, 2007 From the Instituto Mexicano de la Propriedad Industrial Re. Application No. PA/a/2004/002912.
European Search Report and the European Search Opinion Dated Dec. 30, 2010 From the European Patent Office Re. Application No. 10182948.9.
Examination Report Dated Dec. 5, 2011 From the Instituto Mexicano de la Propriedad Industrial Re. Application No. MX/a/2009/000641 and Its Summary in English.
Examination Report Dated Jun. 8, 2011 From the Instituto Mexicano de la Propriedad Industrial Re. Application No. MX/a/2007/015511 and Its Summary Into English.
Examination Report Dated Jun. 16, 2011 From the Instituto Mexicano de la Propriedad Industrial Re. Application No. PA/a/2006/010924 and Its Summary in English.
Examination Report Dated Jan. 19, 2012 From the Instituto Mexicano de la Propriedad Industrial Re. Application No. MX/a/2007/015511 and Its Translation Into English.
Examination Report Dated Sep. 20, 2010 From the Instituto Mexicano der la Propriedad Industrial Re. Application No. MX/a/2007/015511 and Its Translation Into English.
Examination Report Dated Aug. 25, 2010 From the Instituto Mexicano de la Propriedad Industrial Re. Application No. PA/a/2004/002912 and Its Summary in English.
Examination Report Dated May 30, 2011 From the Instituto Mexicano de la Propriedad Industrial Re. Application No. PA/a/2004/002912 and Its Summary in English.
Examination Report Dated Dec. 31, 2012 From the Government of India, Patent Office, Intellectual Property Building Re. Application No. 2042/CHENP/2008.
Examiner's Report Dated May 23, 2007 From the Government of India Patent Office Re.: Application No. 642/CHENP/2004-SPS.
Examiner's Report Dated May 2, 2007 From the Australian Government, IP Australia Re.: Application No. 2004201240.
Examiner's Report Dated Jun. 7, 2012 From the Australian Government, IP Australia Re. Application No. 2006256369.
Examiner's Report Dated Oct. 7, 2011 From the Australian Government, IP Australia Re. Application No. 2007274583.
Examiner's Report Dated Jan. 19, 2012 From the Australian Government, IP Australia Re. Application No. 2006256369.
Examiner's Report Dated Oct. 21, 2010 From the Australian Government, IP Australia Re. Application No. 2006256369.
Examiner's Report Dated Feb. 24, 2010 From the Australian Government, IP Australia Re.: Application No. 2008243147.
International Preliminary Report on Patentability Dated Dec. 3, 2007 From the International Preliminary Examining Authority Re.: Application No. PCT/IL2006/000666.
International Preliminary Report on Patentability Dated Sep. 7, 2012 From the International Bureau of WIPO Re. Application No. PCT/IB2011/000915.
International Preliminary Report on Patentability Dated Oct. 12, 2006 From the International Bureau of WIPO Re.: Application No. PCT/IL2005/000341.

(56) References Cited

OTHER PUBLICATIONS

International Preliminary Report on Patentability Dated Oct. 17, 2007 From the International Preliminary Examining Authority Re.: Application No. PCT/IL2006/000666.
International Preliminary Report on Patentability Dated Jun. 21, 2012 From the International Bureau of WIPO Re. Application No. PCT/IL2010/01041.
International Preliminary Report on Patentability Dated Aug. 26, 2010 From the International Bureau of WIPO Re. Re. Application No. PCT/IL2009/000158.
International Preliminary Report on Patentability Dated Jan. 29, 2009 From the International Bureau of WIPO Re.: Application No. PCT/IL2007/000902.
International Preliminary Report on Patentability Dated Jan. 29, 2009 From the International Bureau of WIPO Re.: Application No. PCT/IL2007/000903.
International Search Report and the Written Opinion Dated Dec. 1, 2011 From the International Searching Authority Re. Application No. PCT/IB2011/000915.
International Search Report and the Written Opinion Dated Dec. 3, 2007 From the International Searching Authority Re.: Application No. PCT/IL2006/000666.
International Search Report and the Written Opinion Dated Feb. 8, 2012 From the International Searching Authority Re.: Application No. PCT/IL2011/000752.
International Search Report and the Written Opinion Dated Feb. 12, 2008 From the International Searching Authority Re.: Application No. PCT/IL2007/000903.
International Search Report and the Written Opinion Dated Feb. 13, 2008 From the International Searching Authority Re.: Application No. PCT/IL2007/000902.
International Search Report and the Written Opinion Dated Aug. 23, 2006 From the International Searching Authority Re.: Application No. PCT/IL2005/000341.
International Search Report and the Written Opinion Dated Jun. 25, 2009 From the International Searching Authority Re. Application No. PCT/IL2009/000158.
International Search Report and the Written Opinion Dated Mar. 30, 2011 From the International Searching Authority Re. Application No. PCT/IL2010/01041.
International Search Report Dated Jul. 11, 2003 From the International Searching Authority Re.: Application No. PCT/IL02/00795.
Interview Summary Dated May 6, 2011 From the US Patent and Trademark Office Re. U.S. Appl. No. 12/656,048.
Interview Summary Dated Jan. 27, 2011 From the US Patent and Trademark Office Re.: U.S. Appl. No. 12/585,021.
Invitation to Pay Additional Fees Dated Jun. 13, 2006 From the International Searching Authority Re.: Application No. PCT/IL2005/000341.
Invitation to Pay Additional Fees Dated Nov. 20, 2007 From the International Searching Authority Re.: Application No. PCT/IL2007/000902.
Invitation to Pay Additional Fees Dated Nov. 27, 2007 From the International Searching Authority Re.: Application No. PCT/IL2007/000903.
Notice of Allowance Dated Dec. 1, 2011 From the US Patent and Trademark Office Re. U.S. Appl. No. 12/764,124.
Notice of Allowance Dated Jul. 10, 2009 From the US Patent and Trademark Office Re.: U.S. Appl. No. 11/636,599.
Notice of Allowance Dated Mar. 11, 2008 From the US Patent and Trademark Office Re.: U.S. Appl. No. 10/808,541.
Notice of Allowance Dated Apr. 12, 2012 From the US Patent and Trademark Office Re. U.S. Appl. No. 12/373,542.
Notice of Allowance Dated May 17, 2012 From the US Patent and Trademark Office Re. U.S. Appl. No. 12/656,048.
Notice of Allowance Dated Mar. 21, 2011 From the US Patent and Trademark Office Re.: U.S. Appl. No. 12/585,021.
Notice of Allowance Dated Sep. 21, 2012 From the US Patent and Trademark Office Re. U.S. Appl. No. 13/034,453.
Notice of Allowance Dated Feb. 23, 2012 From the US Patent and Trademark Office Re. U.S. Appl. No. 12/867,055.
Notice of Allowance Dated May 29, 2009 From the US Patent and Trademark Office Re.: U.S. Appl. No. 12/005,342.
Notice of Allowance Dated May 30, 2012 From the US Patent and Trademark Office Re. U.S. Appl. No. 12/309,361.
Notice of the Reason for Rejection Dated Mar. 26, 2010 From the Korean Intellectual Property Office Re.: Application No. 2004-7004581. Korean Only.
Office Action Dated Mar. 2, 2011 From the Israel Patent Office Re. Application No. 196538 and Its Translation Into English.
Office Action Dated Mar. 2, 2011 From the Israeli Patent Office Re. Application No. 196538.
Office Action Dated Jun. 6, 2010 From the Israeli Patent Office Re.: Application No. 161083 and Its Translation Into English.
Office Action Dated Aug. 8, 2008 From the Patent Office of the People's Republic of China Re.: Application No. 02823600.9.
Office Action Dated Aug. 9, 2012 From the Israel Patent Office Re. Application No. 196538 and Its Translation Into English.
Office Action Dated Sep. 9, 2005 From the Patent Office of the People's Republic of China Re.: Application No. 02823600.9 and Its Translation Into English.
Office Action Dated Dec. 12, 2011 From the Israel Patent Office Re.: Application No. 187892 and Its Translation Into English.
Office Action Dated Feb. 14, 2008 From the Government of India Patent Office Re.: Application No. 642/CHENP/2004-SPS.
Office Action Dated Aug. 15, 2012 From the Israel Patent Office Re. Application No. 202291 and Its Translation Into English.
Office Action Dated Feb. 15, 2009 From the Israeli Patent Office Re.: Application No. 161083 and Its Translation Into English.
Office Action Dated May 15, 2008 From the Government of India Patent Office Re.: Application No. 642/CHENP/2004-SPS.
Office Action Dated May 17, 2011 From the Israel Patent Office Re.: Application No. 187892 and Its Translation Into English.
Office Action Dated Aug. 23, 2010 From the Israel Patent Office Re. Application No. 203058 and Its Translation Into English.
Office Action Dated Jun. 24, 2011 From the State Intellectual Property Office of the People's Republic of China Re. Application No. 200780033294.6 and Its Translation Into English.
Office Action Dated Apr. 25, 2010 From the Israel Patent Office Re.: Application No. 187892 and Its Translation Into English.
Office Action Dated Feb. 27, 2009 From the Israeli Patent Office Re.: Application No. 161083 and Its Translation Into English.
Office Action Dated Jul. 27, 2010 From the Israel Patent Office Re.: Application No. 199877 and Its Translation Into English.
Official Action Dated Feb. 1, 2007 From the US Patent and Trademark Office Re.: U.S. Appl. No. 10/808,541.
Official Action Dated Nov. 1, 2011 From the US Patent and Trademark Office Re. U.S. Appl. No. 11/921,578.
Official Action Dated Feb. 2, 2012 From the US Patent and Trademark Office Re. U.S. Appl. No. 12/656,048.
Official Action Dated May 3, 2012 From the US Patent and Trademark Office Re. U.S. Appl. No. 11/921,578.
Official Action Dated Aug. 5, 2011 From the US Patent and Trademark Office Re. U.S. Appl. No. 12/764,124.
Official Action Dated Jan. 6, 2011 From the US Patent and Trademark Office Re. U.S. Appl. No. 12/656,048.
Official Action Dated Jul. 12, 2011 From the US Patent and Trademark Office Re. U.S. Appl. No. 11/921,578.
Official Action Dated Dec. 14, 2010 From the US Patent and Trademark Office Re.: U.S. Appl. No. 12/585,021.
Official Action Dated Mar. 14, 2011 From the US Patent and Trademark Office Re. U.S. Appl. No. 12/764,124.
Official Action Dated Feb. 16, 2010 From the US Patent and Trademark Office Re.: U.S. Appl. No. 12/585,021.
Official Action Dated May 16, 2008 From the US Patent and Trademark Office Re.: U.S. Appl. No. 11/636,594.
Official Action Dated Feb. 17, 2009 From the US Patent and Trademark Office Re.: U.S. Appl. No. 11/636,599.
Official Action Dated Jun. 17, 2010 From the US Patent and Trademark Office Re.: U.S. Appl. No. 12/585,021.
Official Action Dated May 17, 2012 From the US Patent and Trademark Office Re. U.S. Appl. No. 13/034,453.

(56) References Cited

OTHER PUBLICATIONS

Official Action Dated Jun. 19, 2008 From the US Patent and Trademark Office Re.: U.S. Appl. No. 11/636,599.
Official Action Dated Oct. 21, 2011 From the US Patent and Trademark Office Re. U.S. Appl. No. 12/373,542.
Official Action Dated Nov. 22, 2011 From the US Patent and Trademark Office Re. U.S. Appl. No. 12/309,361.
Official Action Dated Jan. 24, 2013 From the US Patent and Trademark Office Re. U.S. Appl. No. 13/531,673.
Official Action Dated Aug. 25, 2011 From the US Patent and Trademark Office Re. U.S. Appl. No. 12/656,048.
Official Action Dated Jul. 25, 2006 From the US Patent and Trademark Office Re.: U.S. Appl. No. 10/808,541.
Official Action Dated Jan. 31, 2012 From the US Patent and Trademark Office Re. U.S. Appl. No. 12/309,361.
Official Action Dated Jan. 31, 2012 From the US Patent and Trademark Office Re. U.S. Appl. No. 13/034,453.
Official Action Dated Oct. 31, 2008 From the US Patent and Trademark Office Re.: U.S. Appl. No. 12/005,342.
Patent Examination Report Dated Jul. 31, 2012 From the Australian Government, IP Australia Re. Application No. 2007274583.
Requisition by the Examiner Dated Aug. 2, 2011 From the Canadian Intellectual Property Office Re. Application No. 2,461,663.
Requisition by the Examiner Dated Aug. 2, 2011 From the Canadian Intellectual Property Office Re. Application No. 2,560,905.
Requisition by the Examiner Dated Feb. 4, 2013 From the Canadian Intellectual Property Office Re. Application No. 2,560,905.
Requisition by the Examiner Dated Jan. 8, 2013 From the Canadian Intellectual Property Office Re. Application No. 2,461,663.
Requisition by the Examiner Dated Nov. 8, 2010 From the Canadian Intellectual Property Office Re. Application No. 2,461,663.
Requisition by the Examiner Dated Apr. 13, 2012 From the Canadian Intellectual Property Office Re. Application No. 2,461,663.
Requisition by the Examiner Dated May 16, 2012 From the Canadian Intellectual Property Office Re. Application No. 2,560,905.
Requisition by the Examiner Dated Aug. 31, 2012 From the Canadian Intellectual Property Office Re. Application No. 2,610,838.
Response Dated May 1, 2006 to Official Action of Mar. 30, 2006 From the US Patent and Trademark Office Re.: U.S. Appl. No. 10/808,541.
Response Dated Sep. 1, 2010 to Office Action of Apr. 25, 2010 From the Israel Patent Office Re.: Application No. 187892.
Response Dated Aug. 2, 2011 to Office Action of Mar. 2, 2011 From the Israeli Patent Office Re. Application No. 196538.
Response Dated Dec. 3, 2007 to Official Action of Feb. 1, 2007 From the US Patent and Trademark Office Re.: U.S. Appl. No. 10/808,541.
Response Dated Mar. 3, 2010 to Official Action of February 16, 2010 From the US Patent and Trademark Office Re.: U.S. Appl. No. 12/585,021.
Response Dated Oct. 3, 2011 to Examination Report of Jun. 8, 2011 From the Instituto Mexicano de la Propriedad Industrial Re. Application No. MX/a/2007/015511.
Response Dated Oct. 3, 2011 to Office Action of Jun. 6, 2010 From the Israeli Patent Office Re.: Application No. 161083.
Response Dated May 5, 2011 to Requisition by the Examiner of Nov. 8, 2010 From the Canadian Intellectual Property Office Re. Application No. 2,461,663.
Response Dated Oct. 5, 2010 to Official Action of Jun. 17, 2010 From the US Patent and Trademark Office Re.: U.S. Appl. No. 12/585,021.
Response Dated Jul. 6, 2011 to Official Action of Mar. 14, 2011 From the US Patent and Trademark Office Re. U.S. Appl. No. 12/764,124.
Response Dated Jun. 6, 2010 to Office Action of Jan. 29, 2010 From the State Intellectual Property Office of the People's Republic of China Re.: Application No. 200680029378.8.
Response Dated Jun. 6, 2011 to Official Action of Jan. 6, 2011 From the US Patent and Trademark Office Re. U.S. Appl. No. 12/656,048.
Response Dated Sep. 7, 2011 to Official Action of Jul. 12, 2011 From the US Patent and Trademark Office Re. U.S. Appl. No. 11/921,578.
Response Dated Nov. 8, 2010 to Office Action of Jul. 12, 2010 From the State Intellectual Property Office of the People's Republic of China Re. Application No. 200780033294.6.
Response Dated Feb. 9, 2011 to Office Action of Aug. 11, 2010 From the State Intellectual Property Office of the People's Republic of China Re. Application No. 200810190781.X.
Response Dated Mar. 9, 2011 to Official Action of Dec. 14, 2010 From the US Patent and Trademark Office Re.: U.S. Appl. No. 12/585,021.
Response Dated Jan. 13, 2010 to Notice for Reason for Rejection of Oct. 20, 2009 From the Japanese Patent Office Re.: Application No. 2003-530202.
Response Dated Jan. 13, 2010 to Office Action of Jul. 17, 2009 From the State Intellectual Property Office of the People's Republic of China Re.: Application No. 200580017025.1.
Response Dated Oct. 13, 2008 to Official Action of Sep. 16, 2008 From the US Patent and Trademark Office Re.: U.S. Appl. No. 12/005,342.
Response Dated Dec. 14, 2011 to Notice of Reason for Rejection of Sep. 30, 2011 From the Japanese Patent Office Re. Application No. 2007-504560.
Response Dated Dec. 15, 2011 to Examiner's Report of Oct. 21, 2010 From the Australian Government, IP Australia Re. Application No. 2006256369.
Response Dated Nov. 15, 2006 to Official Action of Jul. 25, 2006 From the US Patent and Trademark Office Re.: U.S. Appl. No. 10/808,541.
Response Dated Jun. 16, 2011 to Communication Pursuant to Article 94(3) EPC of Dec. 16, 2010 From the European Patent Office Re. Application No. 02772790.8.
Response Dated Nov. 16, 2010 to Examination Report of Aug. 25, 2010 From the Instituto Mexicano de la Propriedad Industrial Re. Application No. PA/a/2004/002912.
Response Dated Feb. 18, 2011 to Examination Report Dated Sep. 20, 2010 From the Instituto Mexicano der la Propriedad Industrial Re. Application No. MX/a/2007/015511 and Its Translation Into English.
Response Dated Jan. 18, 2011 to Notice of Reason for Rejection of Nov. 2, 2010 From the Japanese Patent Office Re. Application No. 2007-504560.
Response Dated Sep. 18, 2011 to Examination Report of Jun. 16, 2011 From the Instituto Mexicano de la Propriedad Industrial Re. Application No. PA/a/2006/010924.
Response Dated Oct. 19, 2011 to Official Action Dated Aug. 5, 2011 From the US Patent and Trademark Office Re. U.S. Appl. No. 12/764,124.
Response Dated Dec. 20, 2010 to Notice of the Reason for Rejection of Oct. 28, 2010 From the Korean Itellectual property Office Re. Application No. 2010-7016372.
Response Dated Jul. 20, 2011 to Notice of Final Rejection of May 30, 2011 From the Korean Intellectual Property Office Re. Application No. 2010-7016372.
Response Dated Aug. 22, 2011 to Office Action of Jun. 24, 2011 From the State Intellectual Property Office of the People's Republic of China Re. Application No. 200780033294.6.
Response Dated Mar. 22, 2011 to Final Notice of the Reason for Rejection of Nov. 24, 2010 From the Korean Intellectual Property Office Re.: Application No. 2009-7024590.
Response Dated Aug. 23, 2011 to Official Action of Jun. 23, 2011 From the US Patent and Trademark Office Re. U.S. Appl. No. 12/373,542.
Response Dated Dec. 23, 2010 to Office Action of Aug. 23, 2010 From the Israel Patent Office Re. Application No. 203058.
Response Dated Feb. 23, 2011 to Examiner's Report of Feb. 24, 2010 From the Australian Government, IP Australia Re.: Application No. 2008243147.
Response Dated Jun. 23, 2010 to Notice of the Reason for Rejection of Feb. 24, 2010 From the Korean Intellectual Property Office Re.: Application No. 2009-7024590.
Response Dated Jun. 23, 2010 to Notice of the Reason for Rejection of Mar. 26, 2010 From the Korean Intellectual Property Office Re.: Application No. 2004-7004581.
Response Dated Nov. 23, 2009 to Office Action of Jul. 23, 2009 From the Israel Patent Office Re.: Application No. 199877.

(56) References Cited

OTHER PUBLICATIONS

Response Dated Oct. 23, 2011 to Office Action Dated May 17, 2011 From the Israel Patent Office Re.: Application No. 187892.
Response Dated Feb. 24, 2009 to Official Action of Oct. 31, 2008 From the US Patent and Trademark Office Re.: U.S. Appl. No. 12/005,342.
Response Dated Jul. 24, 2011 to Communication Pursuant to Article 94(3) EPC of Apr. 11, 2011 From the European Patent Office Re. Application No. 09711260.1.
Response Dated Mar. 24, 2011 to Communication Pursuant to Article 94(3) EPC of Nov. 24, 2010 From the European Patent Office Re. Application No. 07789958.1.
Response Dated Nov. 24, 2011 to Official Action of Aug. 25, 2011 From the US Patent and Trademark Office Re. U.S. Appl. No. 12/656,048.
Response Dated Feb. 25, 2011 to Official Action of Aug. 25, 2010 From the US Patent and Trademark Office Re. U.S. Appl. No. 12/764,124.
Response Dated Jul. 26, 2011 to Official Action of Mar. 14, 2011 From the US Patent and Trademark Office Re. U.S. Appl. No. 12/764,124.
Response Dated Jul. 26 to Communication Pursuant to Rules 70(2) and 70a(2) EPC of Jan. 31, 2011 From the European Patent Office Re. Application No. 10182948.9.
Response Dated Nov. 28, 2010 to Office Action of Jul. 27, 2010 From the Israel Patent Office Re.: Application No. 199877.
Response Dated Dec. 30, 2009 to Office Action of Aug. 31, 2009 From the Israel Patent Office Re.: Application No. 161083.
Restriction Official Action Dated May 9, 2008 From the US Patent and Trademark Office Re.: U.S. Appl. No. 11/636,599.
Restriction Official Action Dated Sep. 16, 2008 From the US Patent and Trademark Office Re.: U.S. Appl. No. 12/005,342.
Restriction Official Action Dated Apr. 17, 2008 From the US Patent and Trademark Office Re.: U.S. Appl. No. 11/636,594.
Restriction Official Action Dated Dec. 19, 2012 From the US Patent and Trademark Office Re. U.S. Appl. No. 13/531,673.
Restriction Official Action Dated Dec. 20, 2011 From the US Patent and Trademark Office Re. U.S. Appl. No. 13/034,453.
Restriction Official Action Dated Jun. 23, 2011 From the US Patent and Trademark Office Re. U.S. Appl. No. 12/373,542.
Restriction Official Action Dated Aug. 25, 2010 From the US Patent and Trademark Office Re. U.S. Appl. No. 12/764,124.
Restriction Official Action Dated Mar. 30, 2006 From the US Patent and Trademark Office Re.: U.S. Appl. No. 10/808,541.
Summons to Attend Oral Proceedings Pursuant to Rule 115(1) EPC Dated Jan. 26, 2012 From the European Patent Office Re. Application No. 06756205.8.
Supplemental After Final Amendment Dated Nov. 17, 2011 in Response to Official Action Dated Aug. 5, 2011 From the US Patent and Trademark Office Re. U.S. Appl. No. 12/764,124.
Supplemental Response Dated Mar. 31, 2009 to Response of Feb. 24, 2009 From the US Patent and Trademark Office Re.: U.S. Appl. No. 12/005,342.
Supplementary European Search Report Dated Apr. 25, 2006 From the European Patent Office Re.: Application No. 02772790.8.
Translation of Decision on Rejection Dated May 30, 2012 From the State Intellectual Property Office of the People's Republic of China Re.: Application No. 200580017025.1.
Translation of Final Notice of the Reason for Rejection Dated Nov. 24, 2010 From the Korean Intellectual Property Office Re.: Application No. 2009-7024590.
Translation of Final Notice of the Reason for Rejection Dated Aug. 31, 2011 From the Korean Intellectual Property Office Re. Application No. 2010-7016372.
Translation of Notice for Reason for Rejection Dated Oct. 20, 2009 From the Japanese Patent Office Re.: Application No. 2003-530202.
Translation of Notice of Final Rejection Dated May 30, 2011 From the Korean Intellectual Property Office Re. Application No. 2010-7016372.
Translation of Notice of Final Rejection Dated May 30, 2011 From the Korean Intellectual Property Office Re.: Application No. 2009-7024590.
Translation of Notice of Reason for Rejection Dated Nov. 2, 2010 From the Japanese Patent Office Re. Application No. 2007-504560.
Translation of Notice of Reason for Rejection Dated Aug. 7, 2012 From the Japanese Patent Office Re. Application No. 2010-008725.
Translation of Notice of Reason for Rejection Dated Nov. 9, 2012 From the Japanese Patent Office Re. Application No. 2011-20274.
Translation of Notice of Reason for Rejection Dated Feb. 10, 2009 From the Japanese Patent Office Re.: Application No. 2003-530202.
Translation of Notice of Reason for Rejection Dated Jul. 20, 2012 From the Japanese Patent Office Re. Application No. 2009-520129.
Translation of Notice of Reason for Rejection Dated Jan. 22, 2013 From the Japanese Patent Office Re. Application No. 2008-515378.
Translation of Notice of Reason for Rejection Dated Nov. 29, 2011 From the Japanese Patent Office Re. Application No. 2008-515378.
Translation of Notice of Reason for Rejection Dated Sep. 30, 2011 From the Japanese Patent Office Re. Application No. 2007-504560.
Translation of Notice of the Reason for Rejection Dated Jun. 1, 2012 From the Korean Patent Office Re. Application No. 2012-7002565.
Translation of Notice of the Reason for Rejection Dated Feb. 24, 2010 From the Korean Intellectual Property Office Re.: Application No. 2009-7024590.
Translation of Notice of the Reason for Rejection Dated Aug. 26, 2009 From the Korean Intellectual Property Office Re.: Application No. 2004-7004581.
Translation of Notice of the Reason for Rejection Dated Mar. 26, 2010 From the Korean Intellectual Property Office Re.: Application No. 2004-7004581.
Translation of Notice of the Reason for Rejection Dated Oct. 28, 2010 From the Korean Intellectual Property Office Re. Application No. 2010-7016372.
Translation of Office Action Dated Jul. 3, 2012 From the State Intellectual Property Office of the People's Republic of China Re.: Application No. 200680029378.8.
Translation of Office Action Dated Nov. 3, 2011 From the State Intellectual Property Office of the People's Republic of China Re.: Application No. 200580017025.1.
Translation of Office Action Dated Jan. 5, 2012 From the State Intellectual Property Office of the People's Republic of China Re. Application No. 200810190781.X.
Translation of Office Action Dated Sep. 10, 2012 From the State Intellectual Property Office of the People's Republic of China Re. Application No. 200810190781.X.
Translation of Office Action Dated Aug. 11, 2010 From the State Intellectual Property Office of the People's Republic of China Re. Application No. 200810190781.X.
Translation of Office Action Dated Jul. 12, 2010 From the State Intellectual Property Office of the People's Republic of China Re. Application No. 200780033294.6.
Translation of Office Action Dated Jul. 17, 2009 From the State Intellectual Property Office of the People's Republic of China Re.: Application No. 200580017025.1.
Translation of Office Action Dated Feb. 23, 2012 From the State Intellectual Property Office of the People's Republic of China Re. Application No. 200780033294.6.
Translation of Office Action Dated Jan. 29, 2010 From the State Intellectual Property Office of the People's Republic of China Re.: Application No. 200680029378.8.
Translation of Office Action Dated Jan. 30, 2012 From the State Intellectual Property Office of the People's Republic of China Re.: Application No. 200680029378.8.
Translation of Decision of Rejection Dated Jul. 6, 2012 From the Japanese Patent Office Re. Application No. 2008-515378.
Written Opinion Dated Feb. 13, 2008 From the International Searching Authority Re.: Application No. PCT/IL2007/000902.
Written Opinion Dated Aug. 23, 2006 From the International Searching Authority Re.: Application No. PCT/IL2005/000341.
Written Opinion Dated Jun. 25, 2009 From the International Searching Authority Re. Application No. PCT/IL2009/000158.

(56) References Cited

OTHER PUBLICATIONS

Bastin et al. "Salt Selection and Optimisation Procedures for Pharmaceutical New Chemical Entities", Organic Process Research & Development, 4: 427-435, 2000.
BioLineRx "BioLineRx Announces Positive Topline Results for BL-1020, A First in Class GABA Enhanced Antipsychotic for the Treatment of Schizophrenia. BL-1020 Meets Primary and Secondary Efficacy Endpoints From the Pahase 2b EAGLE Trial", BioLine Rx, 4 P., Sep. 14, 2009.
Bousquet et al. "Synthesis, Physical Properties, Toxicological Studies and Bioavailability of L-Pyroglutamic and L-Glutamic Acid Esters of Paracetamol as Potentially Prodrugs", Journal of Pharmacy and Pharmacology, 48: 479-485, Jan. 1996.
Bryson et al. "Amitriptyline. A Review of Its Pharmacological Properties and Therapeutic Use in Chronic Pain States", Drug & Aging , 8(6): 459-476, 1996.
Budavari et al. "The Merck Index", Merck & Co., USA, XP002381834, 12th Ed., 1996. p. THER-8, First Col., 6th Line From the Bottom, 2nd Col., Line 13.
Budavari et al. "The Merck Index", Merck & Co., USA, XP002381799, 12th Ed, 1996, p. 1260. p. 1260, § 1.
Budavari et al. "The Merck Index", Merck & Co., USA, XP002381798, 12th Ed., 1996, p. 1246. p. 1246, Last §.
Capasso et al. "Anticonvulsive Activity of A New GABA Mimetic Drug", European Neuropsychopharmacology, 7: 57-63, 1997.
Carducci et al. "Phenylbutyrate Induces Apoptosis in Human Prostate Cancer and Is More Potent Than Phenylacetate", Clinical Cancer Research, XP002613699, 2(2): 379-387, 1996. Abstract.
Chan et al. "Phenothiazine Inhibitors of Trypanothione Reductase as Potential Antitrypanosomal and Antileishmanial Drugs", Journal of Medicinal Chemistry, 41(2): 148-156, 1998.
Cinatl Jr. et al. "Induction of Differentiation and Suppression of Malignant Phenotype of Human Neuroblastoma BE(2)-C Cells by Valproic Acid: Enhancement by Combination With Interferon-Alpha", International Journal of Oncology, 20(1): 97-106, Jan. 2002.
Coradini et al. "Effect of Sodium Butyrate on Human Breast Cancer Cell Lines", Cell Proliferation, XP002613698, 30(3-4) Mar. 1997. Abstract.
Degrand et al. "Synthesis of Nitroxides for Use as Procationic Labels and Their Incorporation Into Nafion Films", The Journal of Organic Chemistry, 58(9): 2573-2577, 1993.
Dutta et al. "Existing Dopaminergic Therapies for Parkinson's Disease", Expert Opinion on Therapeutic Patents, XP002531574, 16: 1613-1625, 2006. § [04.1], Fig.1.
Fingl et al. "General Principles", The Pharmacological Basis of Therapeutics, Chap. 1: 1-46, 1975.
Florence et al. "Prolongation of the Action of Intramuscular Formulations of Phenothiazines", Optimization of Drug Delivery, 17th Alfred Benzon Symposium, Mungsgaard, Copenhagen, p. 93-111, 1982.
Geyer et al. "Animal Behavior Models of the Mechanisms Underlying Antipsychotic Atypicality", Progress in Neuro-Psychopharmacology & Biological Psychiatry, 27: 1071-1079, 2003.
Gil-Ad et al. "Novel Anti-Psychotics That Display GABAergic Acitivity and Decreased Extrapyramidal Side Effects, for the Treatment of Schizophrenia and Related Psychiatric Disorders", Neural Plasticity, XP008064103, 10(3): 200, 2003. Abstract.
Hadad et al. "Pharmacokinetic Analysis and Antiepileptic Activity of N-Valproyl Derivatives of GABA and Glycine", Pharmaceutical Research, XP008038069, 112(6): 905-910, Jan. 1, 1995. Abstract, p. 906, Compound IV, p. 909, r-h Col., § 1.
Koepf-Maier et al. "An Organoid Culture Assay (OCA) for Determining the Drug Sensitivity of Human Tumors", International Journal of Cancer, 51: 99-107, 1992.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
Luo "Pharmacokinetic Studies of Fluphenazine and Four Ester Prodrugs", A Thesis Submitted to the College of Graduate Studies and Research in Partial Fulfillment of the Requirements for the Degree of Doctor of Philosophy in the College of Pharmacy and Nutrition, University Saskatchewan, Saskatoon, Saskatchewan, Canada, p. 1-171, Mar. 1999. p. 5, § 1.2.1.1, p. 19, Compounds, p. 39, § 3.2.2.0, p. 147-152.
Luo et al. "Comparative Pharmacokinetic Analysis of Fluphenazine and Four Ester Prodrugs", Pharmaceutical Research, XP008130430, 14(11 Suppl.): S360, #2441, Nov. 1997. & Annual Meeting of the American Association of Pharmaceutical Scientists, Boston, MA, USA, Nov. 2-6, 1997.
McCaffrey et al. "A Rapid Fluorometric DNA Assay for the Measurement of Cell Density and Proliferation in Vitro", In Vitro Cellular Development Biology, 24(3): 247-252, 1988. Abstract.
Merck "Schizophrenia", the Merck Manuals, Section Psychiatric Disorders, 17th Ed.: 1569-1575, Dec. 10, 1999. Japanese Version and Its Translation Into English. p. 1572, Right Col., Line 15-p. 1573, Left Col., Line 11, p. 1574, Table 193-1.
Milovic et al. "Effect of Structural Analogues of Propionate and Butyrate on Colon Cancer Cell Growth", International Journal of Colorectal Disease, XP002613700, 15(5-6): 264-270, 2000. Abstract, p. 267, Table 2.
Morissette et al. "High-Througput Crystallization: Polymorphs, Salts, Co-Crystals and Solvates of Pharmaceutical Solids", Advanced Drug Delivery Reviews, 56: 275-300, 2004.
Napolitano et al. "New Directions in Parkinson's Research and Treatment", Expert Opinion on Therapeutic Patents, XP002531575, 8:1251-1268, 1998. Fig.4.
Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, XP001027786, 58(8): 1229-1236, Oct. 15, 1999. Abstract, p. 1231, r-h Col., § 2—p. 1232, l-h Col., § 2.
Ogiso et al. "Pharmacokinetic Analysis of Phenytoin and Its Derivatives in Plasma and Brain in Rats", Biological and Pharmaceutical Bulletin, XP002613683, 16(10): 1025-1030, Oct. 1, 1993. Fig.1, Compound 3, p. 1025, l-h Col., § 1, r-h Col., § 1.
Pouzet et al. "Effects of the 5-HT7 Receptor Antagonist SB-258741 in Animal Models for Schizophrenia", Pharmacology, Biochemistry and Behavior, 71: 655-665, 2002.
Quadri et al. "Effects of Centrally Acting Drugs on Serum Prolactin Levels in Rhesus Monkeys", Neuroendocrinology, 27(3-4): 136-147, 1978. Abstract.
Rephaeli et al. "Gamm-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.
Rephaeli et al. "Observation of Sequence-Dependent Interaction Between Prodrugs of Carboxylic-Acid-Esters and Doxorubicin in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.
Sakamoto et al. "Studies on Prodrugs. VI. Preparation and Characterization of 95-Substituted 2-Oxo-1,3-Dioxol-4-yl)Methyl Esters of Mecillinam", Chemical and Pharmaceutical Bulletin, XP008078018, 35(2): 642-646, 1987. Abstract.
Scriba "Phenytoin-Lipid Conjugates as Potential Prodrugs of Phenytoin", Archiv der Pharmazie, VCH—Verlagsgesellschaft MBH, Weinheim, DE, XP001023947, 326(8): 477-481, 1993. Scheme 1, p. 147.
Scriba et al. "Anticonvulsant Activity of Phenytoin-Lipid Conjugates, A New Class of Phenytoin Prodrugs", Journal of Pharmaceutical Pharmacology, XP008064305, 47: 197-203, 1996. Scheme 1, p. 198, Abstract.
Scriba et al. "Synthesis and Anticovulsant Activity of N-Benzyloxycarbonyl-Amino Acid Prodrugs of Phenytoin", Journal of Pharmacy and Pharmacology, XP008069882, 51(5): 549-553, May 1, 1999. Abstract, Fig. 1.

(56) References Cited

OTHER PUBLICATIONS

Shalitin et al. "The Effect of Angiotensin II on Myosin Heavy Chain Expression in Cultured Myocardial Cells", In Vitro Cellular Development Biology—Animal, 32: 573-578, 1996.
Stahl et al. [Ed.] "A Procedure for Salt Selection and Optimization", (by Michael Bowker), Handbook of Pharmaceutical Salts, Chap.7: 161-189, 2002.
Toth "A Novel Chemical Approach to Drug Delivery: Lipidic Amino Acid Conjugates", Journal of Drug Targeting, XP00900873, 2(3): 217-239, 1994. p. 223, col. II, 3rd §.
Unknown "New Edition of Pharmaceutics", People's Hygiene Publishing House, 14: 178, 1998. Abstract in Chinese Only!
Velazquez et al. "Butyrate Inhibits Seeding and Growth of Colorectal Metastases to the Liver in Mice", Surgery, XP005473855, 120(2): 440-448, Aug. 1, 1996. Abstract.
Vezin et al. "Biological Active Poly(N-Metacryloyl-?-Amino Acid) Esters of Fluphenazine and Their Duration of Activity", Journal of Pharmacy and Pharmacology, British Pharmacology Conference 1979, 31(Suppl.): 63P, 1979.
Ware et al. "An Automated Approach to Salt Selection for New Unique Trazodone Salts", Pharmaceutical Research, XP007902093, 21(1): 177-184, 2004. Abstract.
Wilson et al. "Central Nervous System Depressant", Wilson and Gisvold's Textbook of Organic Medicinal and Pharmaceutical Chemistry, 8th Ed., p. 362-371, 1982.
Wolffe "Transcriptional Control. Sinful Repression", Nature, 387: 16017, 1997.
Worms et al. "Dopamine-Like Activities of An Aminopyridazinde Derivative, CM 30366: A Behavioural Study", Naunyn-Schmiedeberg's Archives of Pharmacology, 334: 246-252, 1986.
Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, XP002392213, 17: 2325-2327, 2003. Abstract.
Zaugg et al. "Modification of Hemoglobin With Analogs of Aspirin", The Journal of Biological Chemistry, 255(7): 2816-2821, 1980.
Examination Report Dated Jun. 24, 2013 From the Government of India, Patent Office, Intellectual Property Building Re. Application No. 3906/CHENP/2006.
Hearing Notice Dated Jan. 22, 2014 From the Government of India, Patent Office, Intellectual Property Building Re. Application No. 2042/CHENP/2008.
Notification of Office Action Dated Feb. 19, 2014 From the State Intellectual Property Office of the People's Republic of China Re. Application No. 201180020723.2 and Its Tranlsation Into English.
Grzesiak et al. "Comparison of the Four Anhydrous Polymorphs of Carbamazepine and the Crystal Structure of Form I", Journal of Pharmaceutical Sciences, 92(11): 2260-2271, Nov. 2003.
Communication Pursuant to Article 94(3) EPC Dated Feb. 10, 2014 From the European Patent Office Re. Application No. 11746937.9.
Official Action Dated Jun. 5, 2014 From the US Patent and Trademark Office Re. U.S. Appl. No. 13/604,718.
Lynch "Antidepressants as Analgesics: A Review of Randomized Controlled Trials", Journal of Psychiatry and Neuroscience, 26(1): 30-36, 2001.
Rosen et al. "The Effect of Gamma-Hydroxybutric Acid on Naloxone-Precipitated Opiate Withdrawal", Neuropsychopharmacology, 14(3): 187-193, 1996.
Official Action Dated Mar. 10, 2014 From the US Patent and Trademark Office Re. U.S. Appl. No. 12/963,959.
Harvard College "The Negaitve Symptoms of Schizophrenia", The Harvard Medical School Family Health Guide, President & Fellows of Harvard College, 1 P., 2006.
Notice of Reexamination Dated Nov. 8, 2013 From the Patent Reexamination Board of State Intellectual Property Office of the People's Republic of China Re. Application No. 200580017025.1 and Its Translation Into English.
Notice of the Reason for Rejection Dated Oct. 25, 2013 From the Korean Intellectual Property Office Re. Application No. 10-2009-7003169 and Its Translation Into English.

\* cited by examiner

ACID ADDITION SALT OF A NORTRIPTYLINE-GABA CONJUGATE AND A PROCESS OF PREPARING SAME

RELATED APPLICATIONS

This application is a National Phase of PCT Patent Application No. PCT/IL2011/000752 having International filing date of Sep. 22, 2011, which claims the benefit of priority under 35 USC §119(e) of U.S. Provisional Patent Application No. 61/385,164 filed on Sep. 22, 2010. The contents of the above applications are all incorporated by reference as if fully set forth herein in their entirety.

FIELD AND BACKGROUND OF THE INVENTION

The present invention, in some embodiments thereof, relates to pharmacology, and more particularly, but not exclusively, to a novel acid addition salt of a nortriptyline-GABA conjugate, a novel crystalline form of the acid addition salt, to processes of preparing the same and to uses thereof.

Psychotropic drugs are pharmacological agents that act mainly in the central nervous system (CNS) by modulating neuronal signals transduction. Psychotropic drugs are therefore known, and are referred to herein, as pharmacological agents that exert an activity in the CNS to thereby treat various CNS associated impairments, and include, for example, anti-psychotic drugs, anti-depressants, anti-convulsants, anxiolytics, inhibitors of brain-derived enzymes and the like.

The administration of psychotropic drugs is typically associated with adverse side effects, such as seizures, headaches, fatigue, hyperactivity, dizziness, and many more, which severely limit their use. A comprehensive list of such side effects can be found, for example, in "The Merck Manual of Medical Information" (Merck & Co. Inc.).

The prior art teaches the use of GABA agonists (including GABA itself) as potential agents for reducing neuroleptic-induced side effects.

A series of conjugates of psychotropic drugs and organic acids and their use in the treatment of psychotropic and/or proliferative disorders and diseases and for chemosensitization are described in detail in International Patent Applications published as WO 03/026563 and WO 2005/092392 and in U.S. patent application having Publication No. 20040242570, which are all incorporated by reference as if fully set forth herein.

Acid addition salts of such conjugates in which the organic acid has a free amino group (such as in GABA and other GABA agonists) have been disclosed in WO 2006/000666.

A nortriptyline-GABA conjugate (nortriptyline-4-aminobutyrate; BL-1021) has been described in, for example, U.S. Pat. No. 7,619,006 and was further reported to have a beneficial therapeutic effect in the treatment of pain in, for example, WO 2008/010223, which is incorporated by reference as if fully set forth herein.

Crystalline forms, that include polymorphs and pseudopolymorphs, are distinct solids sharing the same structural formula, yet having different physical properties due to different conformations and/or orientations of the molecule in the unit cell of the crystal. The physical characteristics, such as solubility and stability, of different crystalline forms are often different and are thus relevant in the field of pharmacology.

For a general review of crystalline forms (i.e. polymorphs and pseudopolymorphs) and the pharmaceutical applications of crystalline forms see Wall *Pharm. Manuf.* 1986, 3, 33; Haleblian et al. *J. Pharm. Sci.* 1969, 58, 911; and Haleblian *J. Pharm. Sci.*, 1975, 64, 1269.

SUMMARY OF THE INVENTION

In the course of further studies conducted in view of the beneficial pharmacological effect of a conjugate of nortriptyline and γ-aminobutyric acid, the present inventors have designed a novel synthetic pathway for scaled-up preparation of this conjugate, have prepared an acid addition salt of this conjugate and have further uncovered that an exemplary such acid addition salt of this conjugate may be obtained as a crystalline form thereof.

According to an aspect of some embodiments of the present invention there is provided an acid addition salt of nortriptyline-4-aminobutyrate.

According to an aspect of some embodiments of the present invention there is provided a fumaric acid addition salt of nortriptyline-4-aminobutyrate.

According to an aspect of some embodiments of the present invention there is provided a crystalline form of a fumaric acid addition salt of nortriptyline-4-aminobutyrate, characterized by at least one of:

(a) an X-Ray Powder Diffraction (XRPD) pattern exhibiting at least four of the peaks shown in FIG. 3 (or any other characterization of the crystal structure, as described hereinbelow);

(b) an infrared spectrum exhibiting at least three of the absorption peaks shown in FIG. 1; and (c) a Differential Scanning Calorimetry (DSC) exhibiting an endothermic peak maximum that ranges from 155° C. to 160° C.

According to some embodiments of the invention, the crystalline form of nortriptyline-4-aminobutyrate fumarate is characterized by an X-Ray Powder Diffraction (XRPD) pattern exhibiting at least six of the peaks shown in FIG. 3.

According to some embodiments of the invention, the crystalline form of nortriptyline-4-aminobutyrate fumarate as described herein is characterized by an X-Ray Powder Diffraction (XRPD) pattern exhibiting at least seven of the peaks shown in FIG. 3.

According to some embodiments of the invention, the crystalline form of nortriptyline-4-aminobutyrate fumarate as described herein is characterized by an X-Ray Powder Diffraction (XRPD) pattern substantially identical to the XRPD pattern shown in FIG. 3.

According to some embodiments of the invention, the crystalline form of nortriptyline-4-aminobutyrate fumarate as described herein is characterized by an infrared spectrum exhibiting at least five of the absorption peaks shown in FIG. 1.

According to some embodiments of the invention, the crystalline form of a fumaric acid addition salt of nortriptyline-4-aminobutyrate as described herein is characterized by an infrared spectrum exhibiting absorption peaks substantially identical to the absorption peaks shown in FIG. 1.

According to an aspect of some embodiments of the present invention there is provided a crystalline form of nortriptyline-4-aminobutyrate fumarate, characterized by an X-Ray Powder Diffraction (XRPD) pattern exhibiting at least four of the peaks shown in FIG. 3, or characterized by any of the crystal data provided hereinbelow.

According to some embodiments of the invention, the crystalline form of nortriptyline-4-aminobutyrate fumarate is characterized by an X-Ray Powder Diffraction (XRPD) pattern exhibiting at least six of the peaks shown in FIG. 3.

According to some embodiments of the invention, the crystalline form of nortriptyline-4-aminobutyrate fumarate is characterized by an X-Ray Powder Diffraction (XRPD) pattern exhibiting at least seven of the peaks shown in FIG. 3.

According to some embodiments of the invention, the crystalline form of nortriptyline-4-aminobutyrate fumarate is characterized by an X-Ray Powder Diffraction (XRPD) pattern substantially identical to the XRPD pattern shown in FIG. 3.

According to an aspect of some embodiments of the present invention there is provided a crystalline form of nortriptyline-4-aminobutyrate fumarate characterized by a Differential Scanning Calorimetry (DSC) exhibiting an endothermic peak maximum that ranges from 155° C. to 160° C. (e.g., 157° C.).

According to some embodiments of the invention, the acid addition salt of nortriptyline-4-aminobutyrate or the crystalline form of nortriptyline-4-aminobutyrate fumarate, as described herein, has a purity greater than 99%, as determined by HPLC area percentage measurements.

According to some embodiments of the invention, the acid addition salt of nortriptyline-4-aminobutyrate or the crystalline form of nortriptyline-4-aminobutyrate fumarate, as described herein, has an average particle size smaller than 100 microns.

According to some embodiments of the invention, the acid addition salt of nortriptyline-4-aminobutyrate or the crystalline form of nortriptyline-4-aminobutyrate fumarate, as described herein, is characterized by a surface area higher than 6 $m^2$/gram.

According to some embodiments of the invention, the acid addition salt of nortriptyline-4-aminobutyrate or the crystalline form of nortriptyline-4-aminobutyrate fumarate, as described herein, is characterized by a surface area that ranges from 6 $m^2$/gram to 12 $m^2$/gram.

According to some embodiments of the invention, the crystalline form of fumaric acid addition salt of nortriptyline-4-aminobutyrate as described herein, is obtainable by:

(i) reacting a nortriptyline-4-aminobutyrate with fumaric acid, to thereby obtain the fumaric acid addition salt of nortriptyline-4-aminobutyrate; and (ii) contacting the fumaric acid addition salt of nortriptyline-4-aminobutyrate with diethyl ether.

According to an aspect of some embodiments of the present invention there is provided a process of preparing the crystalline form of fumaric acid addition salt of nortriptyline-4-aminobutyrate of any of claims 4 to 18, the process comprising:

(i) reacting a nortriptyline-4-aminobutyrate with fumaric acid, to thereby obtain the fumaric acid addition salt of nortriptyline-4-aminobutyrate; and (ii) contacting the fumaric acid addition salt of nortriptyline-4-aminobutyrate with diethyl ether, thereby obtaining the crystalline form.

According to some embodiments of the invention, the contacting comprises suspending the fumaric acid addition salt of nortriptyline-4-aminobutyrate in diethyl ether.

According to some embodiments of the invention, the process further comprises re-crystallizing the fumaric acid addition salt of nortriptyline-4-aminobutyrate from a solvent mixture that comprises ethanol, water and diethyl ether.

According to an aspect of some embodiments of the present invention there is provided a process of preparing an acid addition salt of nortriptyline-4-aminobutyrate, the process comprising reacting nortriptyline-4-aminobutyrate with an acid, thereby obtaining the acid addition salt.

According to some embodiments of the invention, the reacting is performed in the presence of a solvent.

According to some embodiments of the invention, the solvent comprises ethanol.

According to some embodiments of the invention, the reacting is performed at room temperature.

According to some embodiments of the invention, the acid is fumaric acid.

According to some embodiments of the invention, the process further comprises, subsequent to the reacting:

isolating the acid addition salt of nortriptyline-4-aminobutyrate.

According to some embodiments of the invention, the isolating comprises contacting the acid addition salt of nortriptyline-4-aminobutyrate with diethyl ether.

According to some embodiments of the invention, the process further comprises recrystallizing acid addition salt of nortriptyline-4-aminobutyrate.

According to some embodiments of the invention, the nortriptyline-4-aminobutyrate is prepared by reacting nortriptyline and N-protected 4-aminobutyric acid, to thereby obtain N-protected nortriptyline-4-aminobutyrate; and removing the N-protecting group.

According to some embodiments of the invention, reacting nortriptyline and N-protected 4-aminobutyrate is performed in the presence of a coupling reagent.

According to some embodiments of the invention, the coupling reagent comprises HOBt (1-Hydroxybenzotriazole).

According to some embodiments of the invention, the coupling reagent further comprises EDAC (1-Ethyl-3-(3-dimethylaminopropyl)carbodiimide).

According to some embodiments of the invention, removing the N-protecting group is performed in the presence of methanesulfonic acid.

According to some embodiments of the invention, any of the processes described herein further comprises milling the acid addition salt of nortriptyline-4-aminobutyrate or the crystalline form of fumarate acid addition salt of nortriptyline-4-aminobutyrate.

According to some embodiments of the invention, the milling results in an average particle size of the acid addition salt of nortriptyline-4-aminobutyrate or of the crystalline form of fumarate acid addition salt of nortriptyline-4-aminobutyrate that is smaller than 100 microns.

According to an aspect of some embodiments of the present invention there is provided a process of large-scale preparation of nortriptyline-4-aminobutyrate, the process comprising reacting nortriptyline and N-protected 4-aminobutyric acid in the presence of a coupling reagent.

According to some embodiments of the invention, the coupling reagent comprises HOBt (1-Hydroxybenzotriazole).

According to some embodiments of the invention, the coupling reagent further comprises a dehydrating agent.

According to some embodiments of the invention, the dehydrating agent comprises EDAC (1-Ethyl-3-(3-dimethylaminopropyl)carbodiimide).

According to some embodiments of the invention, an amount of nortriptyline is at least 20 moles.

According to an aspect of some embodiments of the present invention there is provided a pharmaceutical composition comprising the fumaric acid addition salt of nortriptyline-4-aminobutyrate of claims 1 to 4 or the crystalline form of nortriptyline-4-aminobutyrate fumarate salt of any of claims 4 to 19 and a pharmaceutically acceptable carrier.

According to some embodiments of the invention, the pharmaceutical composition is packaged in a packaging material and identified in print, in or on the packaging material, for use in the treatment of pain.

According to an aspect of some embodiments of the present invention there is provided a fumaric acid addition salt of nortriptyline-4-aminobutyrate or a crystalline form of the nortriptyline-4-aminobutyrate fumarate salt, as described herein, for use in the treatment of pain.

According to an aspect of some embodiments of the present invention there is provided a fumaric acid addition salt of nortriptyline-4-aminobutyrate or a crystalline form of the nortriptyline-4-aminobutyrate fumarate salt, as described herein, for use as a medicament. In some embodiments, the medicament is for the treatment of a CNS disease or disorder. In some embodiments, the medicament is for treating pain.

According to an aspect of some embodiments of the present invention there is provided a use of the fumaric acid addition salt of nortriptyline-4-aminobutyrate or of the crystalline form of the nortriptyline-4-aminobutyrate fumarate salt as described herein in the preparation of a medicament. In some embodiments, the medicament is for the treatment of a CNS disease or disorder. In some embodiments, the medicament is for treating pain.

According to an aspect of some embodiments of the present invention there is provided a method of treating a CNS disease or disorder or pain, the method comprising administering to a subject in need thereof a therapeutically effective amount of the fumaric acid addition salt of nortriptyline-4-aminobutyrate or the crystalline form of the nortriptyline-4-aminobutyrate fumarate salt as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
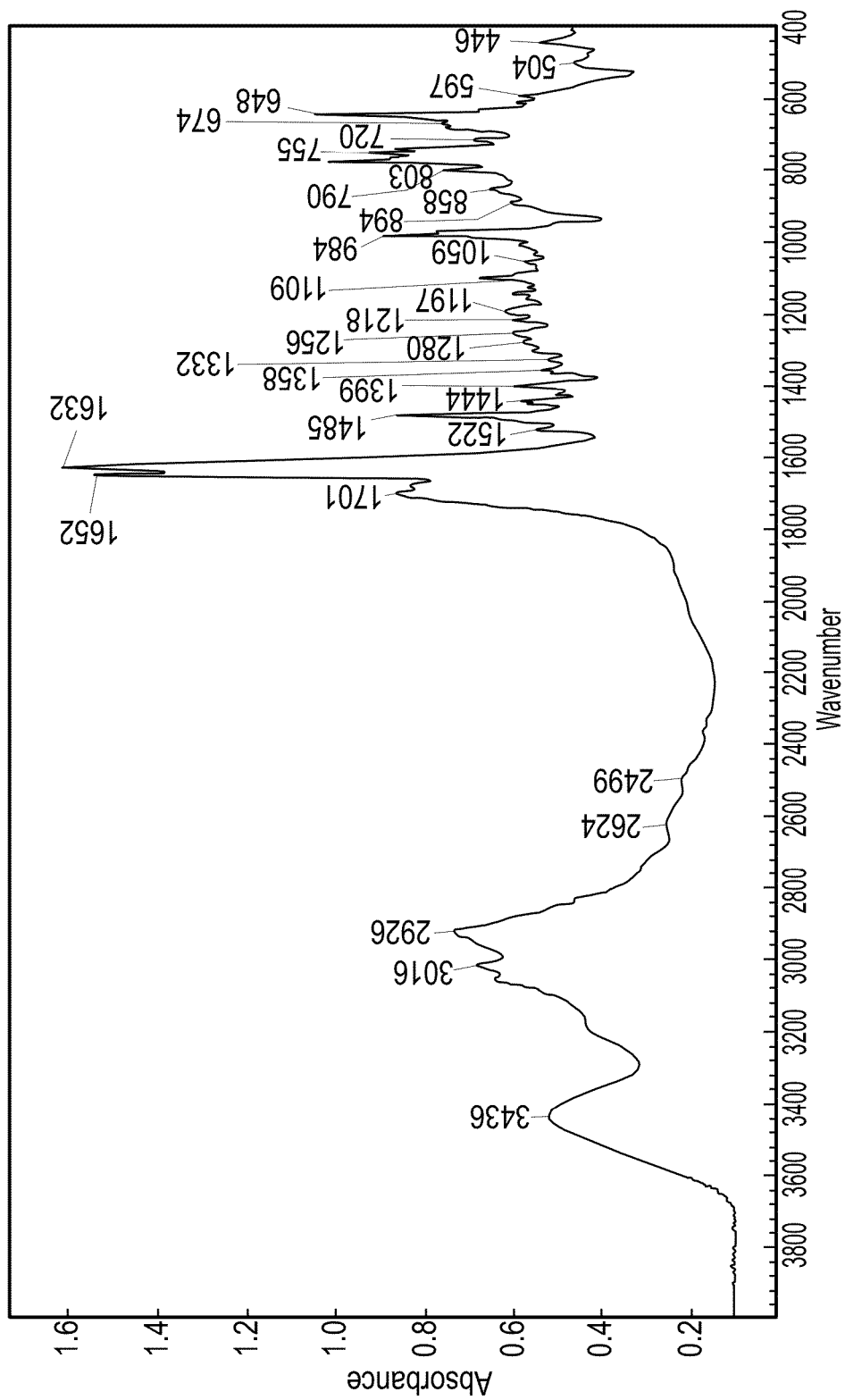
FIG. 1 presents an exemplary FT-IR spectrum of BL-1021 fumarate salt (batch CC-2562.0-01.1)

The present invention, in some embodiments thereof, relates to pharmacology, and more particularly, but not exclusively, to a novel acid addition salt of a nortriptyline-GABA conjugate, a novel crystalline form of the acid addition salt, to processes of preparing the same and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Previous publications teach a conjugate of nortriptyline and γ-aminobutyric acid (GABA) and that such a conjugate exhibits beneficial therapeutic effects, for example in the treatment of pain, and is therefore a promising pharmaceutically active agent.

The present inventors have now prepared an acid addition salt of a conjugate of nortriptyline and γ-aminobutyric acid, and have further uncovered that an exemplary such acid addition salt of this conjugate may be obtained as a crystalline form thereof.

The phrase "chemical conjugate", as used in the context of the present embodiments, refers to a chemical conjugate in which the drug nortriptyline is covalently linked to an organic acid such as 4-aminobutyric acid (GABA) via an amide bond formed between the carboxylic acid group of the organic acid and a free amine group of the nortriptyline, as depicted for a the conjugate nortriptyline-GABA in Scheme 1 in the Examples section that follows.

Herein, the chemical conjugate of nortriptyline and GABA is also referred to herein as nortriptyline-GABA, as nortriptyline-4-aminobutyrate, or as BL-1021.

Hence, according to an aspect of some embodiments of the present invention, there are provided acid addition salts of nortriptyline-4-aminobutyrate.

As is well known in the art, the phrase "acid addition salt" describes a complex of two ionizable moieties, a base and an acid, which, when interacted in a particular stoichiometric proportion and under suitable conditions, form a salt that comprises one or more cations of the base moiety and one or more anions of the acid moiety. As used herein, the phrase "acid addition salt" refers to such a complex as described hereinabove, in which the base moiety in amine, as defined hereinbelow, such that the salt comprises a cationic form of the amine and an anionic form of an acid.

Depending on the stoichiometric proportions between the base and the acid in the salt complex, as is detailed hereinbelow, the acid additions salts can be either mono addition salts or poly addition salts.

The phrase "mono addition salt", as used herein, refers to a salt complex in which the stoichiometric ratio between the acid anion and amine cation is 1:1, such that the acid addition salt includes one molar equivalent of the acid per one molar equivalent of the conjugate.

The phrase "poly addition salt", as used herein, refers to a salt complex in which the stoichiometric ratio between the acid anion and the amine cation is greater than 1:1 and is, for example, 2:1, 3:1, 4:1 and so on, such that the acid addition salt includes two or more molar equivalents of the acid per one molar equivalent of the conjugate.

The stoichiometric proportions between the base and the acid of the salt complex, according to preferred embodiments of the present invention, preferably range from 6:1 to 1:6 base:acid equivalents, more preferably from 4:1 to 1:4 base:acid equivalents, more preferably from 3:1 to 1:3 base:acid equivalents and more preferably from 1:1 to 1:3 base:acid equivalents.

The acid addition salts of a chemical conjugate according to the present invention are therefore complexes formed between one or more amino groups of the drug and one or more equivalents of an acid.

The acid addition salts may include a variety of organic and inorganic acids, such as, but not limited to, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, fumaric acid which affords a fumaric acid addition salt, hydrochloric acid which affords a hydrochloric acid addition salt, maleic acid which affords a maleic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono acid addition salt or a poly acid addition salt, as these terms are defined hereinabove.

According to some embodiments, the acid addition salt is a fumaric acid addition salt of nortriptyline-4-aminobutyrate.

Herein, the phrase "a fumaric acid addition salt of nortriptyline-4-aminobutyrate" is also referred to herein interchangeably as "nortriptyline-4-aminobutyrate fumarate", "nortriptyline-4-aminobutyrate fumarate salt", "nortriptyline-γ-aminobutyrate fumarate," "BL-1021 fumarate salt," or "GABA-nortriptyline fumarate."

According to an aspect of some embodiments of the present invention there is provided a process of preparing an acid addition salt of nortriptyline-4-aminobutyrate, the process comprising reacting nortriptyline-4-aminobutyrate with an acid, to thereby obtain the acid addition salt.

The nortriptyline-4-aminobutyrate can be prepared by methods known in the art (e.g., as described in WO 2008/010223). Optionally and preferably, the nortriptyline-4-aminobutyrate is prepared as described in detail hereinbelow.

The acid reacted with the nortriptyline-4-aminobutyrate is an acid corresponding to the desired acid addition salt, as described hereinabove.

In some embodiments, reacting nortriptyline-4-aminobutyrate with an acid is performed in the presence of a solvent.

The solvent can be an aqueous solvent, an organic solvent or a mixture thereof.

In some embodiments, the solvent comprises an organic solvent.

Organic solvents include, but are not limited to, polar solvents, non-polar solvents, protic solvents and aprotic solvents.

In some embodiments, the solvent comprises a polar solvent such as, but not limited to, an alcohol.

In some embodiments, the organic solvent is a water-miscible organic solvent (e.g., short alcohols having 1-3 carbon atoms).

An exemplary suitable solvent is ethanol. Other polar organic solvents and/or protic solvents, or otherwise water-miscible organic solvents are also contemplated.

In some embodiments, reacting the nortriptyline-4-aminobutyrate with the acid is effected by contacting the nortriptyline-4-aminobutyrate with a solution that contains the acid (e.g., an aqueous solution). In some embodiments, the solution of the acid is heated prior to contacting the nortriptyline-4-aminobutyrate. In some embodiments, the solution of the acid is heated to about 70° C.

In some embodiments, a heated solution of the acid is added to a solution containing the nortriptyline-4-aminobutyrate and an organic solvent, as described herein.

Thus, in some embodiments, the solvent comprises an organic solvent (e.g., a water-miscible organic solvent) and water (derived from the aqueous solution containing the acid).

In some embodiments, reacting the nortriptyline-4-aminobutyrate and the acid is performed during a time period that ranges from about 30 minutes to about 2 hours.

In some embodiments, once the addition of the acid is completed, the obtained reaction mixture is cooled to room temperature, and is optionally maintained at this temperature for the remaining reaction time (e.g., for approximately 40 minutes).

In some embodiments, the process comprises isolating the obtained acid addition salt.

In some embodiments, isolating the obtained acid addition salt is effected by precipitating the obtained acid addition salt from the reaction mixture.

In some embodiments, precipitating the obtained acid addition salt is effected by contacting the reaction mixture with a non-polar organic solvent.

Exemplary non-polar organic solvents include, but are not limited to, ethers (e.g., diethyl ether, methyl-t-butyl ether, THF), and alkanes (e.g., hexanes).

An exemplary suitable non-polar solvent is an ether such as diethyl ether. Other non-polar and/or water immiscible organic solvents are also contemplated.

The acid addition salt can optionally be subjected to recrystallization, either prior to, or subsequent to, being isolated.

In some embodiments, the resulting acid addition salt is isolated and is then further subjected to recrystallization.

By "recrystallization" it is meant a process which comprises solvating a reaction product and thereafter causing the material to crystallize. General techniques for the recrystallization of compounds are known to those skilled in the art. Such techniques include, for example, crystallization from solvents, thermal treatment and sublimation. It is often impossible to predict, a priori and without experimentation, which procedure, process or regime will provide good crystallization of a given compound.

In some embodiments, the acid is fumaric acid and the acid addition salt is nortriptyline-4-aminobutyrate fumarate, as described herein.

In some embodiments, recrystallization of the fumaric acid salt is effected as described hereinbelow for obtaining a crystalline form of the fumaric acid salt of the chemical conjugate.

While reducing the present invention to practice, the present inventors have further prepared and characterized a crystalline form of the fumaric acid addition salt of nortriptyline-4-aminobutyrate.

Thus, according to an aspect of some embodiments of the present invention, there is provided a crystalline form of a fumaric acid addition salt of nortriptyline-4-aminobutyrate.

In some embodiments, the crystalline form is characterized by unique X-Ray powder diffraction pattern; a unique infrared spectrum and/or a characteristic endothermic peak, measured by DSC.

Figure 3:
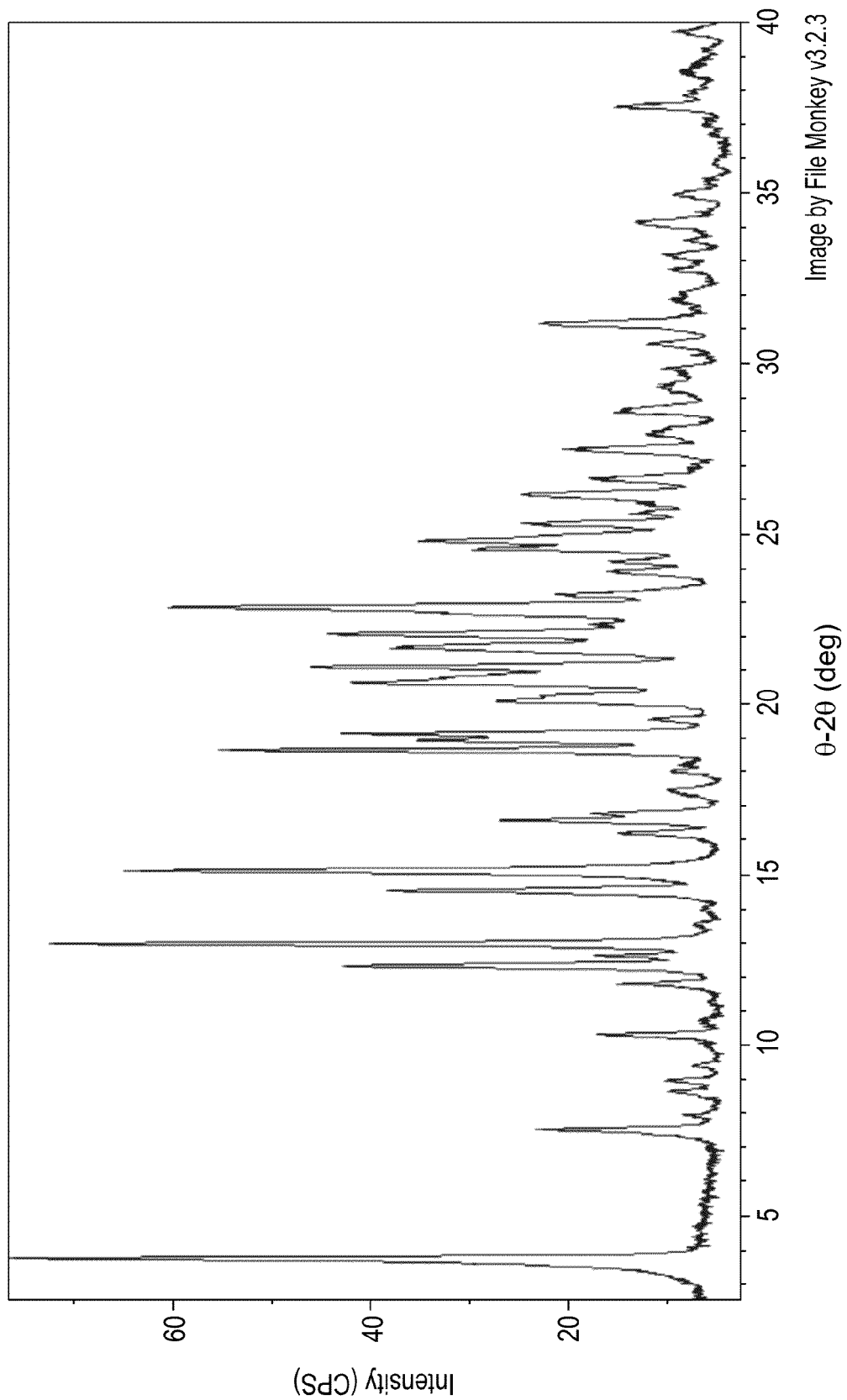
FIG. 3 presents an exemplary XRPD pattern obtained from milled crystalline BL-1021 fumarate salt (batch CC-2562.0-01.1)

Thus, in some embodiments, the crystalline form is characterized by at least one of:

(a) an X-Ray Powder Diffraction (XRPD) pattern exhibiting at least four of the peaks shown in FIG. 3;

(b) an infrared spectrum exhibiting at least three of the absorption peaks shown in FIG. 1; and (c) a Differential Scanning Calorimetry (DSC) exhibiting an endothermic peak maximum that ranges from 155° C. to 160° C. (e.g., at about 157° C.).

As used herein, the term "about" (e.g., as, for example, in the context of "an endothermic peak") describes ±10%, or ±5%, or ±5° C., or ±2° C.

It is to be noted that the data obtained in DSC measurements depend in part on the instrument used and the environmental conditions at the time measurements are effected (e.g., humidity). It is to be also noted that the temperature value of an endothermic peak maximum described herein refers to the temperature value at which maximal heat flux is observed, while in effect, peak onset can be between 5° C., 10° C. or 20° C. lower. It is to be further noted that the endothermic peak onset, as measured in DSC measurements, is often considered as the melting point of a tested sample.

Accordingly, an endothermic peak maximum of the fumaric acid addition salt of nortriptyline-4-aminobutyrate can be, for example, at any value ranging from 130° C. to 190° C., and thus can be, for example, 135° C., 140° C., 145° C., 150° C., 152° C., 153° C., 154° C., 155° C., 156° C., 157° C., 158° C., 159° C., 160° C., 165° C., 170° C., 175° C., 180° C. or 185° C. In some embodiments, an endothermic peak maximum of the fumaric acid addition salt of nortriptyline-4-aminobutyrate can be, for example, at any value ranging from 150° C. to 160° C., or from 155° C. to 160° C. and thus can be, for example, 150° C., 152° C., 153° C., 154° C., 155° C., 156° C., 157° C., 158° C., 159° C., or 160° C. Other values within the range of values indicated herein are also contemplated.

As described in the Examples section that follows, various samples of nortriptyline-4-aminobutyrate fumarate, all prepared under the same synthetic conditions, were subjected to XRPD measurements and all exhibited similar XRPD patterns, which were therefore defined as characteristic of a crystalline form.

As known is the art, each crystalline form of a substance has a characteristic XRPD pattern and equivalency can therefore be determined if substances exhibit XRPD patterns that have at least some of the positional peaks and corresponding relative intensities substantially identical.

A representative XRPD pattern of crystalline nortriptyline-4-aminobutyrate fumarate as described herein is shown in FIG. 3.

In some embodiments, the crystalline form of nortriptyline-4-aminobutyrate fumarate is characterized by an X-Ray Powder Diffraction (XRPD) pattern exhibiting at least five, six, seven or more of the peaks shown in FIG. 3.

Reference to the peaks depicted in FIG. 3 is made for the peak position, namely, for the refraction angle (2θ) at which a peak is observed. Optionally, reference is made also for the relative intensity of a peak observed at a refraction angle.

In some embodiments, the crystalline form of nortriptyline-4-aminobutyrate fumarate is characterized by an X-Ray Powder Diffraction (XRPD) pattern substantially identical to the XRPD pattern shown in FIG. 3.

By "substantially" it is meant that at least 80% of the peaks, at least 85% of the peaks, at least 90% of the peaks, at least 95% of the peaks, at least 98% of the peaks, at least 99% of the peaks or all of the peaks appear at the same refraction angle as in the XRPD pattern presented in FIG. 3. By "substantially" it is also meant that each of these peaks has an intensity which is at least 80%, at least 85%, at least 90%, at least 95%, at least 98%, at least 99%, is the same, or is no more than 101%, 102%, 105%, 110%, 115% or no more than 120%, compared to the intensity of each corresponding peak in the XRPD pattern presented in FIG. 3.

As described in the Examples section that follows, the crystalline form of the fumarate addition salt was further defined as a triclinic system and further, by the dimensions of a cell unit.

Thus, in some embodiments, the crystalline form as described herein has a Unit Cell Occupancy (Z) of 4, and is further characterized as follows:

A unit cell length [a] of about 9.379 Å (e.g., of from 9.37 to 9.39 Å );

A unit cell length [b] of about 11.098 Å (e.g., of from 11.08 to 11.11 Å );

A unit cell length [c] of about 23.568 Å (e.g., of from 23.42 to 23.60 Å );

A cell angle [α] of about 87.24° (e.g., of from 87.1 to 87.4°);

A cell angle [β] of about 87.49° (e.g., of from 87.1 to 87.6°);

A cell angle [γ] of about 89.32° (e.g., of from 89.1 to 87.5°); and

A unit cell volume of about 2447.8 Å $^3$/cell (e.g., of from 2430 to 2460 Å $^3$/cell), and corresponding Z/V values.

In some embodiments, the crystalline form described herein is characterized by unit cell length [abc] as described herein.

In some embodiments, the crystalline form described herein is further characterized by the cell angles [αβγ] as described herein.

In some embodiments, the crystalline form described herein is characterized by a unit cell volume as described herein.

As described in the Examples section that follows, various samples of crystalline nortriptyline-4-aminobutyrate fumarate were subjected to Infra-Red (IR) spectroscopy measurements, and all exhibited similar IR spectra, indicating the same molecular structure and further defining a characteristic IR spectroscopy of the crystalline form.

A representative IR spectrum of the crystalline nortriptyline-4-aminobutyrate fumarate as described herein is shown in FIG. 1.

Thus, according to some embodiments, the crystalline form of a fumaric acid addition salt of nortriptyline-4-aminobutyrate is characterized by an infrared spectrum exhibiting at least three, four, five, six, seven or more of the absorption peaks shown in FIG. 1.

According to some embodiments, the crystalline form of a fumaric acid addition salt of nortriptyline-4-aminobutyrate is characterized by an infrared spectrum exhibiting absorption peaks substantially identical to the absorption peaks shown in FIG. 1.

Reference to the peaks depicted in FIG. 1 is made for the peak position (wavenumber, or cm$^{-1}$).

By "substantially" it is meant that at least 80% of the peaks, at least 85% of the peaks, at least 90% of the peaks, at least 95% of the peaks, at least 98% of the peaks, at least 99% of the peaks or all of the peaks appear at the same position wavenumber, or cm$^{-1}$) as in the representative IR spectrum presented in FIG. 1. According to some embodiments, the crystalline form of nortriptyline-4-aminobutyrate fumarate described in the context of these embodiments has a purity greater than 99%, as determined by HPLC area percentage measurements.

By "HPLC area percentage measurements" it is meant the area percentage of a peak that is identified as corresponding to nortriptyline-4-aminobutyrate fumarate. This term does not necessarily refer to values obtained when performing quantity analysis using HPLC measurements.

As described in detail in the Examples section that follows, several samples of the nortriptyline-4-aminobutyrate fumarate or the crystalline form thereof, as described in the context of the present embodiments, have been analyzed also for their BET surface area, light microscopy and particle size. Most of the tested samples were found to exhibit similar (essentially the same) physicochemical characterizing features.

According to some embodiments, the average particle size of the acid addition salt of nortriptyline-4-aminobutyrate or the crystalline form thereof is smaller than 100 microns.

In some embodiments, the surface area of the acid addition salt of nortriptyline-4-aminobutyrate or of the crystalline form thereof is higher than 6 m$^2$/gram.

In some embodiments, the surface area ranges from 6 m$^2$/gram to 12 m$^2$/gram.

According to some embodiments, the crystalline form of fumaric acid addition salt of nortriptyline-4-aminobutyrate as described herein is obtainable by reacting nortriptyline-4-aminobutyrate with fumaric acid, to thereby obtain the fumaric acid addition salt of nortriptyline-4-aminobutyrate, and contacting the fumaric acid addition salt of nortriptyline-4-aminobutyrate with diethyl ether, as is further detailed hereinafter.

According to another aspect of the present invention, there is provided a process of preparing a crystalline form of the fumaric acid addition salt of nortriptyline-4-aminobutyrate.

The process, according to this aspect of the present invention, is generally effected by reacting nortriptyline-4-aminobutyrate with fumaric acid, to thereby provide the fumaric acid addition salt, and then contacting the fumaric acid addition salt with a solvent as defined hereinafter, to thereby obtain the crystalline form.

Generally, the crystalline form of the fumaric acid addition salt of nortriptyline-4-aminobutyrate is prepared by reacting nortriptyline-4-aminobutyrate with fumaric acid in a solvent or mixture of solvents, to thereby obtain the fumaric acid addition salt of nortriptyline-4-aminobutyrate, and crystallizing the resulting acid addition salt. The type of crystalline form that is produced may be influenced by the solvent or mixture of solvents used in the reaction.

Thus, in some embodiments, the solvent for contacting the fumaric acid addition is selected suitable for providing a crystalline form of the fumaric acid addition salt as described herein.

In some embodiments, the solvent comprises ethanol, water, and diethyl ether.

Thus, in some embodiments, contacting the fumaric acid addition salt with a solvent is effected by utilizing a mixture of solvents.

In some embodiments, the contacting is effected by contacting the fumaric acid addition salt with a non-polar solvent, as described herein.

In some embodiments, the non-polar solvent is diethyl ether.

In some embodiments, contacting the acid addition salt is further effected by recrystallizing the acid addition salt by dissolving it an ethanol-water mixture and then precipitating the acid addition salt by adding a non-polar solvent (e.g., diethylether).

In view of the pharmacological activity of nortriptyline-4-aminobutyrate, it is desired to produce the acid addition salt of nortriptyline-4-aminobutyrate or the crystalline form of nortriptyline-4-aminobutyrate fumarate as described herein in a form suitable for pharmaceutical purposes. One of the parameters that render a pharmaceutically active agent suitable for pharmaceutical purposes is the average particles size thereof and/or the particle size distribution.

Thus, in some embodiments, any of the acid addition salts described herein, as well as the crystalline form of nortriptyline-4-aminobutyrate fumarate as described herein, are further subjected to milling.

The milling can be performed using any milling procedure known in the art. An exemplary milling procedure is described in the Examples section that follows.

In some embodiments, the milling results in an average particle size of the acid addition salt of nortriptyline-4-aminobutyrate or of the crystalline form of fumaric acid addition salt of nortriptyline-4-aminobutyrate that is smaller than 100 microns.

Thus, in some embodiments, the fumaric acid addition salt of nortriptyline-4-aminobutyrate after milling had a particle size up to approximately 400 μm with a $D_{90}$ of 200±25%.

The physicochemical properties of the fumaric acid addition salt of nortriptyline-4-aminobutyrate and/or of the crystalline form of nortriptyline-4-aminobutyrate fumarate salt described herein render these agents highly suitable for use pharmaceutical active agents.

Thus, according to an aspect of some embodiments of the present invention, there is provided a pharmaceutical composition comprising the fumaric acid addition salt of nortriptyline-4-aminobutyrate or the crystalline form of nortriptyline-4-aminobutyrate fumarate salt and a pharmaceutically acceptable carrier.

Hereinafter, the term "pharmaceutically acceptable carrier" describes a carrier or a diluent that does not cause significant irritation to an organism and does not abrogate the biological activity and properties of the administered compound. Examples, without limitations, of carriers are: propylene glycol, cyclodextrins, saline, emulsions and mixtures of organic solvents with water, as well as solid (e.g., powdered) and gaseous carriers.

As used herein a "pharmaceutical composition" refers to a preparation of the fumaric acid addition salt of nortriptyline-4-aminobutyrate or the crystalline form of nortriptyline-4-aminobutyrate fumarate salt described herein (as active ingredient), with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

According to some embodiments, a pharmaceutical composition comprising the fumaric acid addition salt of nortriptyline-4-aminobutyrate or the crystalline form of nortriptyline-4-aminobutyrate fumarate salt, as described herein, and a pharmaceutically acceptable carrier, is packaged in a packaging material and identified in print, in or on said packaging material, for use in the treatment of a CNS disease or disorder.

The crystalline form of the nortriptyline-4-aminobutyrate fumarate salt as described herein can be used in the treatment of any CNS disease or disorder that is treatable by nortriptyline-4-aminobutyrate or a salt thereof.

Exemplary such CNS disorders are disclosed, for example, in U.S. Pat. No. 7,619,006 and in WO 2008/010223.

According to an embodiment of the present invention, the pharmaceutical composition as described herein, is packaged in a packaging material and identified in print, in or on said packaging material, for use in the treatment of pain.

According to an embodiment of the present invention, the fumaric acid addition salt of nortriptyline-4-aminobutyrate or the crystalline form of the nortriptyline-4-aminobutyrate fumarate salt mentioned hereinabove is identified for use in the treatment of a CNS disease or disorder, as described herein.

According to some embodiments of the present invention, the fumaric acid addition salt of nortriptyline-4-aminobutyrate or the crystalline form of the nortriptyline-4-aminobutyrate fumarate salt as described herein, is identified for used in the treatment of pain.

According to some embodiments of the invention, the fumaric acid addition salt of nortriptyline-4-aminobutyrate or the crystalline form of the nortriptyline-4-aminobutyrate fumarate salt as described herein is for use as a medicament.

According to some embodiments of the invention, the medicament is for the treatment of a CNS disease or disorder, as described herein.

According to some embodiments of the invention, the medicament is for the treatment of pain.

Accordingly, according to some embodiments of the invention, there is provided a use of fumaric acid addition salt of nortriptyline-4-aminobutyrate or the crystalline form of the nortriptyline-4-aminobutyrate fumarate salt as described herein, in the preparation of a medicament for the treatment of a CNS disease or disorder, as described herein.

According to some embodiments of the invention, there is provided use of fumaric acid addition salt of nortriptyline-4-aminobutyrate or the crystalline form of the nortriptyline-4-aminobutyrate fumarate salt as described herein, in the preparation of a medicament for the treatment of pain.

According to an aspect of some embodiments of the present invention, there is provided a method of treating CNS disease or disorder, as described herein, which is effected by to a subject in need thereof a therapeutically effective amount of the fumaric acid addition salt of nortriptyline-4-aminobutyrate or the crystalline form of the nortriptyline-4-aminobutyrate fumarate salt as described herein.

According to an aspect of some embodiments of the present invention, there is provided a method of treating pain, which is effected by administering to a subject in need thereof a therapeutically effective amount of the fumaric acid addition salt of nortriptyline-4-aminobutyrate or the crystalline form of the nortriptyline-4-aminobutyrate fumarate salt as described herein.

In any of the methods and uses described herein the fumaric acid addition salt of nortriptyline-4-aminobutyrate or the crystalline form of the nortriptyline-4-aminobutyrate fumarate salt can be utilized either per se or as a part of a pharmaceutical composition as described herein.

The fumaric acid addition salt of nortriptyline-4-aminobutyrate or the crystalline form of the nortriptyline-4-aminobutyrate fumarate salt can be formulated for administration by any of the routes of administration as described herein.

The fumaric acid addition salt of nortriptyline-4-aminobutyrate or the crystalline form of the nortriptyline-4-aminobutyrate fumarate salt can be utilized in combination (by co-administration or co-formulation) with an additional active agent, for example, an additional active pharmaceutically active agent for treating an indicated condition (e.g., a CNS disease or disorder such as pain).

In the course of practicing the preparation of the novel acid addition salts of a nortriptyline-GABA conjugate described herein, a process of preparing the free-base nortriptyline-GABA conjugate in a large-scale has been designed and successfully practiced.

As is well known in the art, development of conditions for a particular reaction performed based upon different quantities or scales of reagents is not trivial. Parameters which may differ depending on the scale upon which the reaction is performed are for example, but not limited to heat management, reaction time, yield, manner of isolation, and purity.

Thus according to an aspect of some embodiments of the present invention there is provided a process of large-scale preparation of nortriptyline-4-aminobutyrate, the process comprising reacting nortriptyline and N-protected 4-aminobutyric acid in the presence of a coupling reagent.

By "large-scale" it is meant that the amount of at least one of the starting materials used in a reaction is 20 moles or more. Preferably, a large-scale synthetic process also yields the final product in an amount of 20 moles or more.

Thus, according to some embodiments of the present invention, the amount of nortriptyline used in the large-scale process described herein is at least 20 moles.

By "N-protected 4-aminobutyric acid" it is meant that the free amino group that is derived from GABA is protected by an N-protecting group (e.g., an amino protecting group). Selecting a suitable N-protecting group is performed while considering the synthetic steps involved in the process, the reagents used and the reaction conditions, and is well within the knowledge of a person skilled in the art.

Non-limiting examples of N-protecting groups that are suitable for use in the context of the present embodiments include benzyloxycarbonyl (CBz), t-butoxycarbonyl (t-BOC), fluorenylmethoxycarbonyl (Fmoc), phthalimides (Pht) and benzenesulfonyl (Ts).

In some embodiments, reacting nortriptyline and N-protected 4-aminobutyrate is performed in the presence of a coupling reagent.

By "coupling reagent" it is meant a chemical species which activates one or more of the reagents thereby rendering it more prone to undergo the coupling step or is used during the course of the reaction in order to remove a molecule or molecules of water (also known as a dehydrating agent).

Coupling agents known in the art are often diimides or triazolols such as, but not limited to, DCC (N,N'-dicyclohexylcarbodiimide), DIC (N,N'-diisopropylcarbodiimide), EDAC (1-ethyl-3-(3-dimethylaminopropyl)carbodiimide), HOBt (1-hydroxy-benzotriazole), and HOAt (1-hydroxy-7-aza-benzotriazole).

In some embodiments, the coupling reagent comprises HOBt (1-Hydroxybenzotriazole).

In some embodiments, the coupling reagent further comprises EDAC (1-Ethyl-3-(3-dimethylaminopropyl)carbodiimide).

Once nortriptyline is reacted with N-protected GABA, a N-protected nortriptyline-GABA conjugate is obtained, and removal of the N-protecting group is effected.

Removing the N-protected group can be performed by any deprotecting means known in the art as suitable for the selected N-protecting group.

In some embodiments, removing the N-protecting group is performed in the presence of methanesulphonic acid. However, other acids are also contemplated. Optionally, the reaction mixture obtained upon addition of MSA is further heated to 30° C. for several hours (e.g. from 10 to 30 hours).

An exemplary successful large-scale process of preparing about 34 moles of the nortriptyline-GABA conjugate is described in Example 1 hereinafter.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods:

All reagents and solvents were obtained from known vendors unless otherwise indicated.

FTIR measurements were performed on a Biorad Excalibur FTS3000MX IR-Spectrophotometer according to USP <197> on a mixture of the test compound and KBr in the range between 4000 and 650 cm$^{-1}$.

HPLC measurements were performed using Dionex HPLC system as follows: samples were diluted in 75:25 (v/v) water: acetonitrile and analyzed by reverse phase HPLC using a Waters XTerra MS C18 column, 5 μm, 250 mm×4.6 mm, eluted isocratic by a 1.59 vol. equivalent 0.1M citric acid+1.0 vol. equivalent 0.2M disodium hydrogen phosphate buffer+ 1.30 vol. equivalent acetonitrile (pH=4.5) (total run time of 60 minutes), and monitored at 240 nm. Retention Time (RT) of BL-1021 was approximately 16.7 minutes.

Differential Scanning Calorimetry (DSC) was performed according to USP <891> using a Shimadzu DSC-50 instrument. The DSC was performed under a nitrogen stream by ramping 5-7 mg of samples up to 250° C. at a ramp rate of 10° C. per minute.

Determination of ROI (Residue On Ignition): The crucible was heated to 600° C. for 30 minutes before use. The crucible was marked and tare weight was determined. Two grams of the material were weighted into the crucible. After addition of 0.5-2 ml concentrated sulfuric acid the material was incinerated. Material burning was strictly avoided. The incineration was performed until no more white vapor was formed. Another 0.5-1 ml concentrated sulfuric acid was added, the crucible was placed in the furnace at 200° C. and the heat was slowly increased to 300° C. Boiling of the sulfuric acid was avoided. After the release of white vapor stopped, the temperature was increased to 600° C. This temperature was maintained until all organic matter was completely burned up. After cooling, the crucible was weighted. Then 0.1-0.5 ml concentrated sulfuric acid was added again and the crucible was heated to 300° C., then the temperature was increased to 600° C. and this temperature was maintained for at least 30 minutes. This was repeated until mass was constant (Δmax <±0.5 mg). A system suitability test was performed with a reference sample (e.g., silicon dioxide) which was heated to 600° C. for at least 30 minutes and stored dry. One gram of a reference sample was weighted in the crucible and treated exactly as described above for the sample.

Heavy metals content was determined using USP <231> Method II.

Amount of residual solvents was determined by GC analyses, on a J & W Scientific, DB-624, 75 meter×0.53 mm, 3 μm film thickness column and HP6890 Gas Chromatography system equipped with FID detector, HP7694 headspace sampler and Dionex Chromeleon software was used for this analysis. The method was validated for the following organic solvents: methanol, ethanol, diethyl ether, dichloromethane, tert-butyl acetate, diisopropylethylamine, dimethylformamide.

Ion content of fumarate and chloride was determined by ion chromatography-suppressed conductivity.

XRPD patterns were collected using a PANalytical XPert Pro diffractor. The specimen was analyzed using Cu Kα radiation produced using an Optix ling fine-focus source. An elliptically graded multilayered mirror was used to focus Cu Kα X-rays of the source through the specimen and onto the detector. The specimen was sandwiched between 3 micron-thick films, analyzed in transmission geometry, and rotated to optimize orientation statistics. A beam-stop was used to minimize the background generated by air scattering. Helium and the anti-scatter extension were not used. Soller slits were used for the incident and diffracted beams to minimize axial divergence. Diffraction patterns were collected using a scanning position-sensitive detector (XCelerator) located 240 mm from the specimen. Prior to the analysis, a silicon specimen (NIST standard reference material 640c) was analyzed to verify the position of the silicon 111 peak.

Polarized light microscopy was performed using a Leica DM LP microscope equipped with Spot Insight color camera (model 3.2.0). A 20× or 40× objective was used with the cross polarizers and a first order red compensator in place to view the sample. Samples were placed on a glass slide, then a cover glass was placed over the sample, and a drop of mineral oil was added. Images were acquired at ambient temperature using Spot software (v.4.5.9 for Windows). Micron bars were inserted onto the images as a reference for particle size.

Surface area data were collected using nitrogen absorption on a BET Micrometics Gemini V (11-point BET analysis) analyzer. The samples were outgassed at 25° C. under vacuum for at least 2 hours. SRM 1899 and SRM 1900 were used as the calibration standards.

Particle size data was acquired using a Malvern Instruments MS2000 equipped with a Hydro2000μP dispersion unit. Data was collected and analyzed with Mastersizer 2000v.5.1 software, using volume based measurements. NIST traceable glass beads were used as the reference standard.

The final method conditions selected for determining the particle size of BL-1021 fumarate salts were as follows:
Dispersant: silicone oil;
Dispersant refractive index: 1.403;
Pump speed: 1750 rpm;
Model: general purpose;
Sensitivity: normal.

Samples were submitted to Particle Technology Labs (PTL), Downers Grove, Ill., for bulk and tapped density analyses.

Example 1

Large-Scale Preparation of Nortriptyline-4-Aminobutyrate (BL-1021)

The synthetic pathway for a large-scale preparation of Nortriptyline-4-aminobutyrate (BL-1021) is depicted in Scheme 1 below.

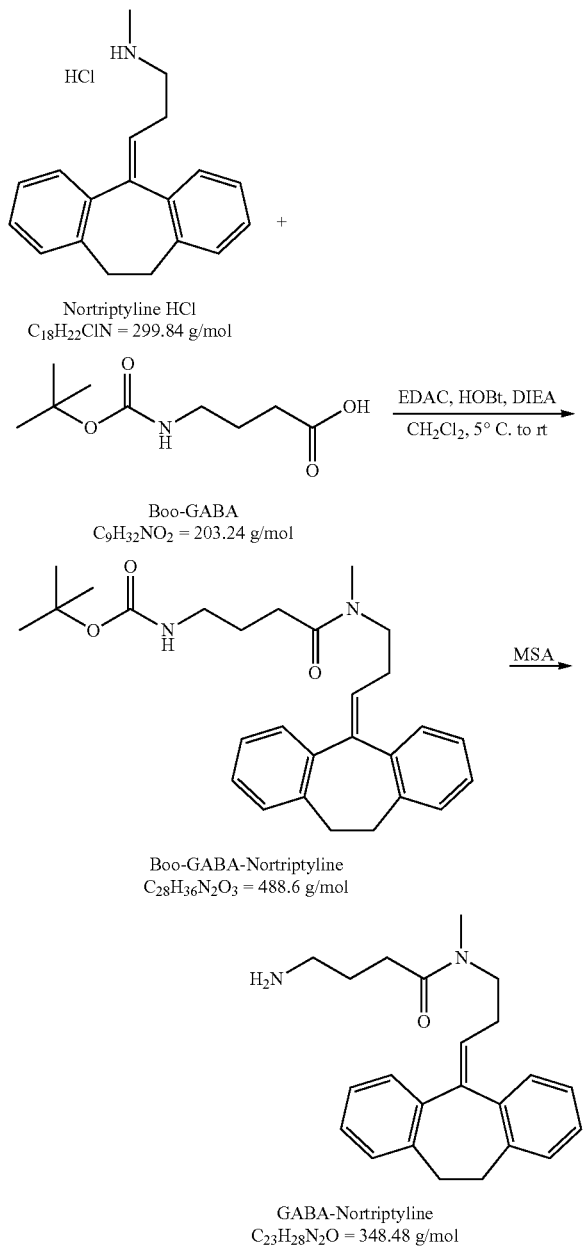

Scheme 1

Nortriptyline HCl
$C_{18}H_{22}ClN$ = 299.84 g/mol

Boc-GABA
$C_9H_{32}NO_2$ = 203.24 g/mol

Boc-GABA-Nortriptyline
$C_{28}H_{36}N_2O_3$ = 488.6 g/mol

GABA-Nortriptyline
$C_{23}H_{28}N_2O$ = 348.48 g/mol

Preparation of N-Boc nortriptyline-4-aminobutyrate

Nortriptyline hydrochloride is reacted with Boc-protected GABA using the following general procedure:

A flask is charged with nortriptyline hydrochloride and Boc-GABA in a non-polar solvent (e.g., dichloromethane (DCM)) and the mixture is stirred until reagents are fully dissolved. A coupling reagent mixture containing 1-Ethyl-3-(3-dimethylaminopropyl)carbodiimide (EDAC), diisopropylethylamine (DIEA) and 1-Hydroxybenzotriazole (HOBt) is then added while cooling to 0±10° C. using a mixture of ice/water/salt as a cooling bath. The reaction mixture is then stirred at room temperature (18±5° C.) for a few hours, while monitoring the reaction progress by TLC and $^1$H NMR. If conversion is not complete, approximately 0.1% of Boc-GABA and coupling reagent (the EDAC, DIEA and HOBt mixture is added to the reaction mixture at −5±5° C. and the reaction is stirred at room temperature (18±5° C.) until completion. Water is then added to the reaction vessel and the pH of the aqueous phase is adjusted to ≤7 by addition of citric acid.

The mixture is thereafter transferred to a separatory funnel and the aqueous layer is removed. The remaining organic layer is washed with 5% citric acid (×3). The white precipitate which forms is removed by filtration. The organic phase is concentrated under reduced pressure to afford an oily solid, which is then dissolved in a mixture of dimethylformamide (DMF) and methanol. Water is added slowly over a period of 2±0.5 hours, and the mixture is then stirred for at least 15 hours to allow the formation of a white precipitate. The solid is then filtered, washed with water, and dried under vacuum. Purity is examined by $^1$H NMR by determination of the ratio of the integral from 7.0-7.3 ppm to the integral from 7.4 ppm and 9.0 ppm. If this ratio is less than 8, an additional recrystallization from DMF, methanol, and water is performed.

In an exemplary large-scale procedure, a flask was charged with nortriptyline hydrochloride (11 kg, 36.7 mol) and Boc-GABA (9.46 kg, 46.5 mol) and dichloromethane (DCM; 49.5 liters) and the mixture was stirred until reagents were fully dissolved. A mixture of 1-ethyl-3-(3-dimethylaminopropyl)carbodiimide (EDAC; 13.31 kg), diisopropylethylamine (DIEA; 23.1 liters) and 1-Hydroxybenzotriazole (HOBt; 9.46 kg) (also referred to herein as a coupling reagent mixture) was then added while cooling to 0±10° C. using a mixture of ice/water/salt as a cooling bath, and the reaction mixture was stirred at room temperature (18±5° C.) for 13 hours, while monitoring the reaction progress by TLC (using a mixture of diethylether:methanol:diisopropylethylamine 2:1:0.05 as eluent) and $^1$H NMR (CDCl$_3$). Water was then added to the reaction vessel and the pH of the aqueous phase was adjusted to ≤7 by addition of citric acid.

The mixture was thereafter transferred to a separatory funnel and the aqueous layer was removed. The remaining organic layer was washed three times with 5% citric acid (1650 grams of citric acid in 33 liters deionized water). After the second extraction, a white precipitate formed and was removed by filtration. The organic phase was concentrated under reduced pressure to afford an oily solid (15.46 kg), which was then dissolved in a mixture of dimethylformamide (DMF; 23.19 liters) and methanol (MeOH; 11.6 liters). Water (46.38 liters) was added slowly over a period of 100 minutes, and the mixture was then stirred for 16 hours to allow the formation of a white precipitate. The solid was thereafter filtered, washed with water, and dried under vacuum to give the N-Boc nortriptyline-4-aminobutyrate (14.41 kg, 88% yield).

The purity of the compound, determined by $^1$H NMR as described hereinabove, was found to be 96%.

Preparation of nortriptyline-4-aminobutyrate

N-Boc nortriptylinenortriptyline-4-aminobutyrate is reacted with methanesulphonic acid using the following general procedure:

A flask is charged with N-Boc nortriptyline-4-aminobutyrate (Boc-GABA-Nortriptyline) and tert-butyl acetate and stirred until reagents are fully dissolved. A solution of methanesulphonic acid in tert-butyl acetate is thereafter added and the obtained reaction mixture is stirred at 30±5° C. for 16±2 hours, while monitoring the reaction progress by $^1$H NMR (measured in CDCl$_3$). The solvent is then evaporated under reduced pressure, and the resulting oily residue is dissolved in dichloromethane (DCM) and a saturated aqueous solution of sodium bicarbonate is added slowly. The pH is adjusted to ≥8 by addition of solid sodium bicarbonate, and the organic layer is removed, the aqueous layer is extracted with dichloromethane (×3), and the combined organic fractions are evaporated under reduced pressure at 40±5° C. to provide GABA-nortriptyline as a beige glassy solid.

In an exemplary procedure, a flask was charged with N-Boc nortriptyline-4-aminobutyrate (Boc-GABA-nortriptyline, 14.41 kg) and tert-butyl acetate (50.40 liters) and stirred until reagents are fully dissolved. A solution of methanesulphonic acid (3.17 liters, 1.5 equivalent) in tert-butyl acetate (3.75 liters) was then added and the obtained reaction mixture was stirred at 30±5° C. for 16±2 hours, while monitoring the reaction progress by $^1$H NMR (measured in CDCl$_3$). The solvent was then evaporated under reduced pressure, the resulting oily residue was dissolved in dichloromethane (DCM; 28.8 liters) and a saturated aqueous solution of sodium bicarbonate (2.163 kg sodium bicarbonate in 21.62 liters deionized water) was thereafter added slowly to the obtained solution. The pH was adjusted to >8 by addition of solid sodium bicarbonate, and the organic layer was removed, the aqueous layer was extracted with dichloromethane (3×9.6 liters), and the combined organic fractions were evaporated under reduced pressure at 40±5° C. for 16±2 hours to provide GABA-nortriptyline (11.82 kg) as a beige glassy solid.

The purity of the compound was determined by $^1$H NMR and was found to be 70%.

Example 2

Preparation of nortriptyline-4-aminobutyrate fumarate salt

Synthesis of nortriptyline-4-aminobutyrate fumarate salt

The synthetic pathway for preparing a fumaric acid addition salt of nortriptyline-4-aminobutyrate, which is also referred to herein interchangeably as BL-1021 fumarate salt, nortriptyline-4-aminobutyrate fumarate and nortriptyline-γ-aminobutyrate fumarate, is depicted in Scheme 2 below.

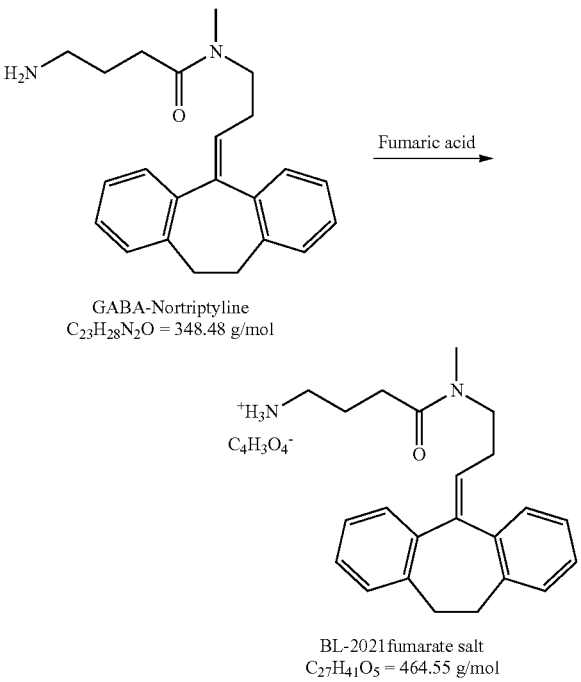

Scheme 2

GABA-Nortriptyline
$C_{23}H_{28}N_2O$ = 348.48 g/mol

BL-2021 fumarate salt
$C_{27}H_{41}O_5$ = 464.55 g/mol

A GABA-nortriptyline conjugate (nortriptyline-4-aminobutyrate, prepared as described in Example 1 hereinabove) is reacted with fumaric acid using the following general procedure:

In a glass reaction vessel, nortriptyline-4-aminobutyrate is dissolved in ethanol (EtOH). In a separate glass reactor, fumaric acid is suspended in ethanol (EtOH) and water and the suspension is heated to 70±5° C. The hot fumaric acid solution is then added to the GABA-Nortriptyline solution and ethanol is added such that the overall ratio of ethanol:water is equal to 90:10. The reaction mixture is stirred for 40±5 minutes while cooling to 25±5° C., and is thereafter filtered and the filtrate is collected. Diethyl ether is added to the filtrate and the obtained solution is stirred for 16±2 hours until a suspension of the product is obtained. This suspension is filtered, and the residue is washed with diethyl ether to give the crude BL-1021 fumarate salt. The crude BL-1021 Fumarate salt is then dissolved in a mixture of ethanol and water (90:10), diethyl ether is added slowly, and the obtained mixture is stirred at room temperature for 20±2 hours to give a suspension of the product. This suspension is filtered and the residue is washed with diethyl ether. The purified product is dried under vacuum for 6 days, during which the material is stirred 1-5 times daily in order to maximize drying efficiency. BL-1021 fumarate salt is obtained as a crystalline white solid.

In an exemplary procedure, nortriptyline-4-aminobutyrate (9 kg) was dissolved in ethanol (EtOH; 5.4 liters) in a glass reaction vessel. In a separate glass reactor, fumaric acid (2.997 kg) was suspended in ethanol (EtOH; 5.4 liters) and water (1.35 liters) and the suspension was heated to 70±5° C. The hot fumaric acid solution was then added to the GABA-Nortriptyline solution and ethanol (1.35 liters) was added such that the overall ratio of ethanol:water was equal to 90:10. The reaction mixture was stirred for 40±5 minutes while cooling to 25±5° C., and was thereafter filtered and the filtrate was collected. Diethyl ether (67.5 liters) was added to the filtrate and the obtained solution was stirred for 16±2 hours until a suspension of the product was obtained. The obtained suspension was filtered, and the residue was washed with diethyl ether (9 liters) to give the crude BL-1021 fumarate salt (7.98 kg). The BL-1021 fumarate salt was then dissolved in a mixture of ethanol and water (90:10 ethanol:water; 15.96 liters, 2 ml of solvent per gram BL-1021 fumarate salt) and diethyl ether (79.76 liters, five times the quantity of the 90:10 ethanol:water mixture) was added slowly, and the resulting mixture was stirred at room temperature for 20±2 hours to give a suspension of the product. This suspension was filtered and the residue was washed with diethyl ether (8 liters). The purified product was dried under vacuum for 6 days, during which the material was stirred 1-5 times daily in order to maximize drying efficiency. BL-1021 fumarate salt was obtained as a crystalline white solid (6.3 kg, 53% yield).

The product's structure was verified by FT-IR and $^1$H-NMR (in d$^6$-DMSO) (data not shown).

The purity of the product was determined by the area percentage of HPLC as 99.7%.

The melting point of the compound was determined by DSC to be 153.4° C.

ROI was determined as 0.2%.

Amount of residual solvents was determined as meeting ICH guidelines for DCM, MeOH (not detected), EtOH (1625 ppm), and Et$_2$O (339 ppm).

Figure 4:
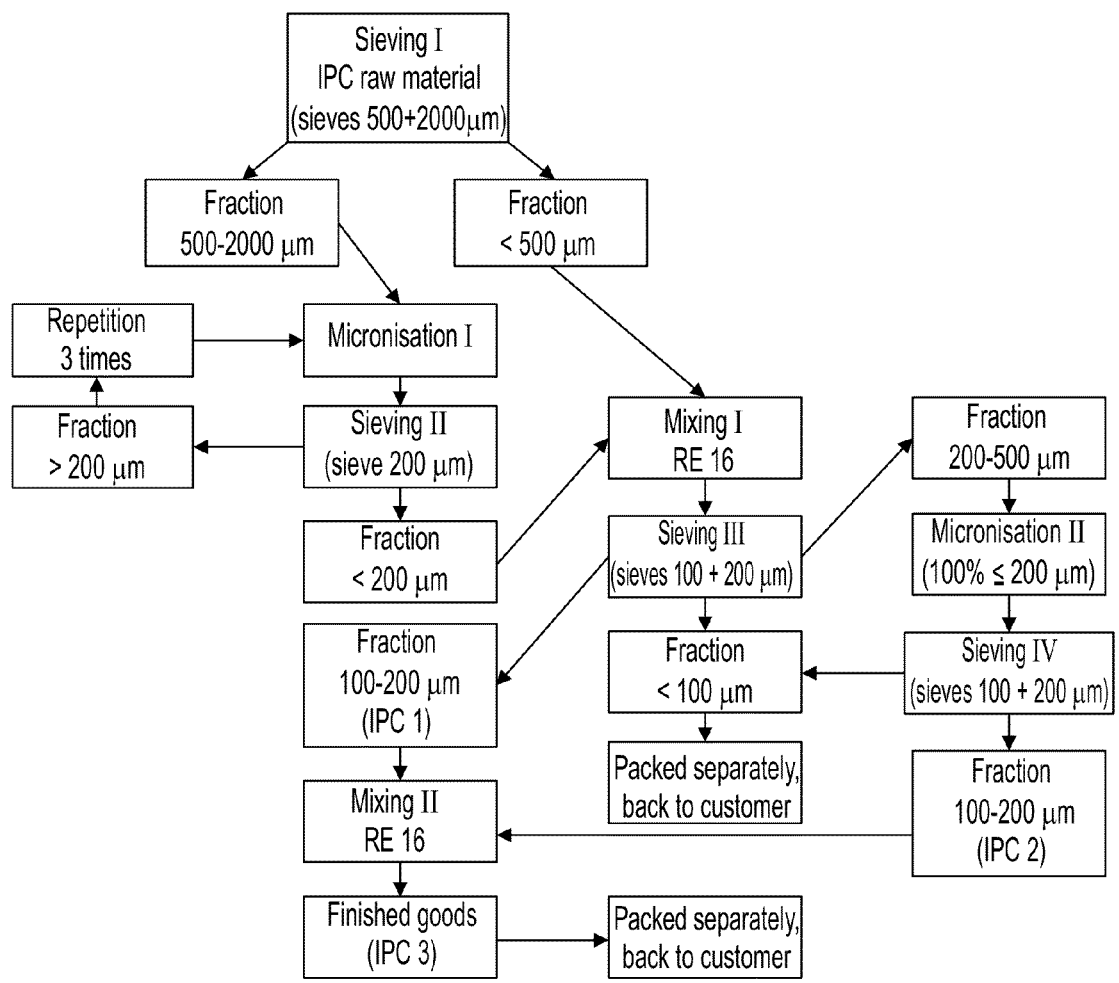
FIG. 4 presents a flow chart describing an exemplary procedure for milling the crystalline BL-1021 fumarate salt.

Milling Process of GABA-Nortriptyline Fumarate Salt:

The purified GABA-nortriptyline fumarate salt obtained as described hereinabove was milled in order to obtain a material with a homogeneous particle distribution with a target D$_{90}$ of 200±20%. FIG. 4 presents a flow chart describing the milling procedure.

Analytical measurements of nortriptyline-4-aminobutyrate fumarate salt were performed after milling, unless otherwise indicated.

FIG. 1 presents an FT-IR spectrum of an exemplary batch of nortriptyline-4-aminobutyrate fumarate salt after being subjected to the above-described milling procedure, and shows that spectral data are consistent with the compound's structure.

The purity of the compound was determined by the area percentage of HPLC as 99.7% (data not shown).

The compound's structure was further verified by $^1$H-NMR (in d$^6$-DMSO) (data not shown). NMR spectra of all batches were similar and consistent with the fumarate salt.

Figure 2:
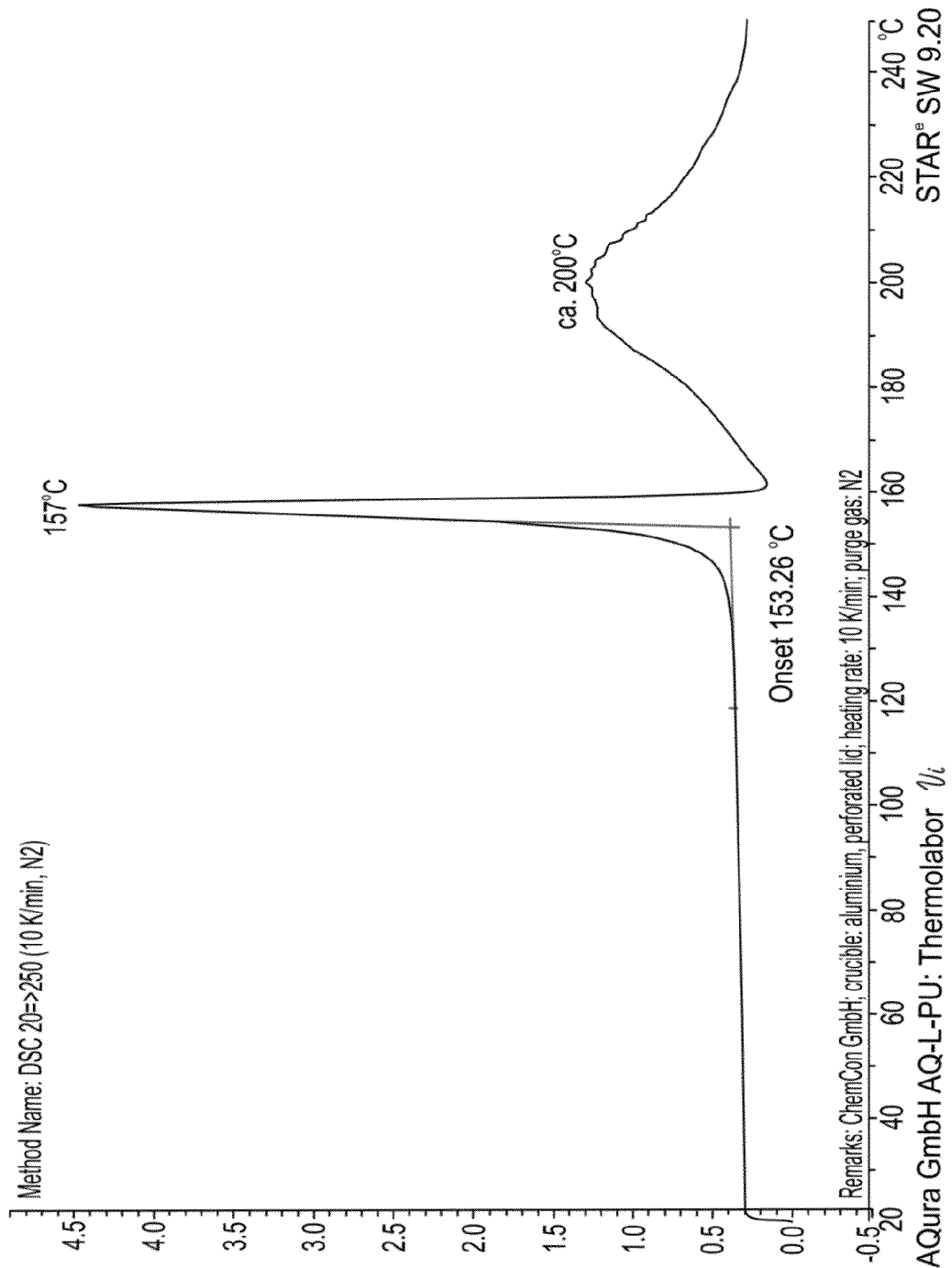
FIG. 2 presents an exemplary DSC curve of crystalline BL-1021 fumarate salt (batch CC-2562.0-01.1), exhibiting an endothermic peak at 153.26° C.

FIG. 2 presents a DSC curve of an exemplary batch of nortriptyline-4-aminobutyrate fumarate salt after being subjected to the above-described milling procedure, showing a melting point of the compound to be 153.6° C. (as the onset temperature), with the maximum of the endothermic peak being 157° C.

ROI was determined as 0.1%.

Amount of residual solvents was determined as meeting ICH guidelines for DCM, MeOH (not detected), EtOH (1508 ppm), and Et$_2$O (312 ppm).

Example 3

Characterization of a Crystalline Form Nortriptyline-4-Aminobutyrate Fumarate Salt Several lots of BL-1021 fumarate salts prepared as described in Example 2 hereinabove were further subjected to X-Ray powder diffraction (XRPD), moisture absorption/desorption (DVS) light microscopy, BET surface area, Malvern particle size and bulk and tapped density analyses, as described in the Methods section hereinabove.

XRPD:

XRPD patterns show that the fumarate salt of nortriptyline-4-aminobutyrate obtained as described hereinabove (see, Example 2) display resolution of reflections which indicate that these lots contain a crystalline material. Further, the obtained XRPD patterns were all similar to one another in terms of peak positions and relative peak intensities, indicating that all tested lots of BL-1021 fumarate salt are the same crystalline form or mixture of forms.

FIG. 3 presents an XRPD pattern of an exemplary batch of BL-1021 fumarate salt.

Interpretation of the XRPD data obtained for BL-1021 fumarate provided the tentative indexing solution of majority crystalline phase and derived quantities. The crystalline system was defined as Triclinic for all tested batches, with exemplary dimensions of the crystal cell unit being as follows:

Unit Cell Occupancy (Z)=4, Unit Cell Length [a,b,c]=9.379 Å ; 11.098 Å and 23.568 Å , respectively, Unit Cell Angles [αβγ]=87.24°, 87.49° and 89.32°, respectively, and Unit cell Volume of 2447.8 Å $^3$/cell. The V/Z value was calculated as 612.0 Å $^3$/asym·unit.

Figure 5:
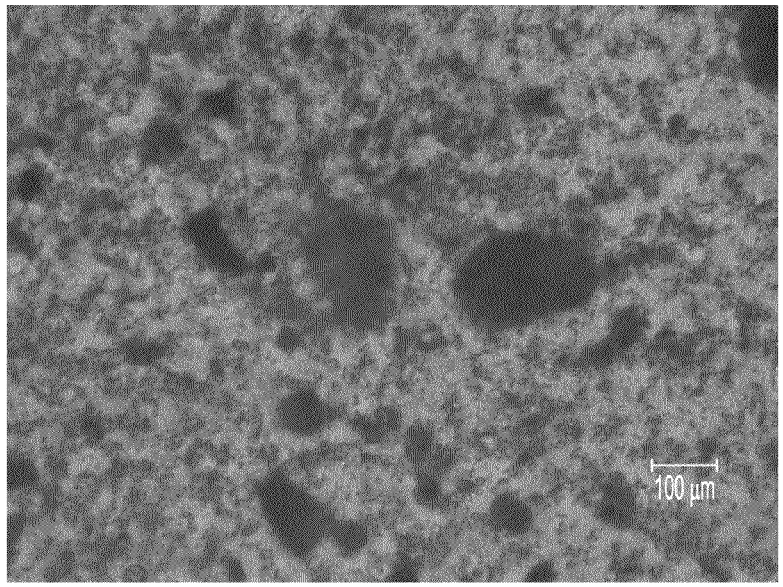
FIG. 5 presents an exemplary image obtained by light microscopy of crystalline BL-1021 fumarate salt.

Light Microscopy Evaluations:

A representative photomicrograph is presented in FIG. 5, showing an image of milled crystalline BL-1021 fumarate salt.

BET Surface Area:

Surface area data obtained for several batches of BL-1021 fumarate salt prepared as described in Example 2 hereinabove, before milling (CC-256.2.0-01) and after milling (CC-2190.0-20.1, CC-2190.0-21.1, CC-2190.0-23.1 and CC-2562.0-01.1) show a surface area that ranges from 7.45 m$^2$/gram to 11.84 m$^2$/gram, after milling as presented in Table 1 below.

TABLE 1

| Lot No. | Results (m$^2$/g) |
| --- | --- |
| CC-256.2.0-01 | 6.58 |
| CC-2190.0-20.1 | 8.43 |
| CC-2190.0-21.1 | 10.84 |
| CC-2190.0-23.1 | 11.84 |
| CC-2562.0-01.1 | 7.45 |

Bulk and Tapped Densities:

The bulk and tapped density data for several batches of BL-1021 fumarate salt prepared as described in Example 2 hereinabove, before milling (Batch No. CC-256.2.0-01) and after milling (Batch Nos. CC-2190.0-20.1, CC-2190.0-21.1, CC-2190.0-23.1 and CC-2562.0-01.1) are presented in Table 2 below, and ranged from 0.18-0.29 gram/ml (bulk) and 0.31-0.42 gram/ml (tap).

TABLE 2

| | Results (g/ml) | |
| --- | --- | --- |
| Lot No. | Bulk density | Tapped density |
| CC-256.2.0-01 | 0.29 | 0.42 |
| CC-2190.0-20.1 | 0.22 | 0.35 |
| CC-2190.0-21.1 | 0.18 | 0.31 |
| CC-2190.0-23.1 | 0.25 | 0.39 |
| CC-2562.0-01.1 | 0.19 | 0.36 |

Particle Size Sample Analysis:

The measurement of particle size of all lots was performed using the same method conditions (silicone oil as a dispersing medium, a pump speed of 1750 rpm). The results of particles size distribution in terms of d10, d50 and d90 values for an exemplary lot are summarized in Table 3 below.

TABLE 3

| Lot No. | d10 | d50 | d90 |
|---|---|---|---|
| CC-2562.0-01 | 7.0 | 93.9 | 220.8 |

Figure 6:
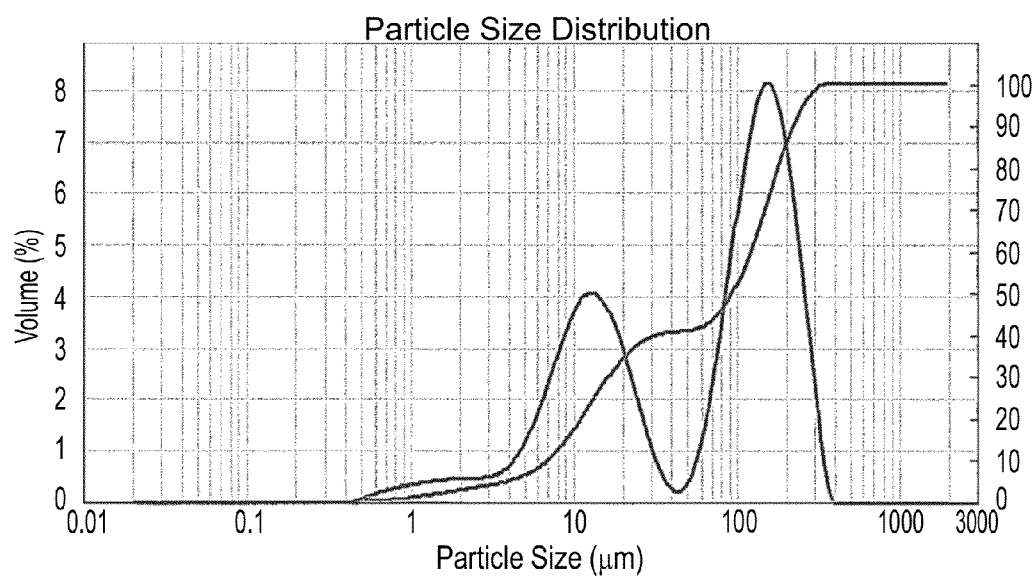
FIG. 6 presents an exemplary particle size distribution graph obtained from milled crystalline BL-1021 fumarate salt (batch CC-2562.0-01.1).

As shown in FIG. 6, the data for lot CC-2562.0-01 showed a bimodal distribution with a fine tail of below 1 µm, and particle size up to approximately 400 µm with a $D_{90}$ of 200±25%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A crystalline form of a fumaric acid addition salt of nortriptyline-4-aminobutyrate, characterized by at least one of:
    (a) an X-Ray Powder Diffraction (XRPD) pattern exhibiting at least four peaks selected from the group of peaks having a refraction angle (2θ) of 3.8; 7.4; 10.2; 12.2; 13.0; 14.5; 15.2; 16.7; 18.6; 18.8; 19.2; 20.0; 20.6; 21.0; 21.7; 22.0; 23.0; 24.5; 24.8; 25.3; 26.1; 27.5; 31.0; and 37.5 degrees;
    (b) an infrared spectrum exhibiting at least three absorption peaks selected from the group consisting of absorption peaks at 2926, 1701, 1652, 1632, 1485, 948, 755, and 648 $cm^{-1}$; and
    (c) a Differential Scanning Calorimetry (DSC) exhibiting an endothermic peak maximum that ranges from 155° C. to 160° C.

2. The crystalline form of nortriptyline-4-aminobutyrate fumarate of claim 1, characterized by an X-Ray Powder Diffraction (XRPD) pattern exhibiting at least six of said peaks.

3. The crystalline form of nortriptyline-4-aminobutyrate fumarate of claim 1, characterized by an X-Ray Powder Diffraction (XRPD) pattern exhibiting at least seven of said peaks.

4. The crystalline form of nortriptyline-4-aminobutyrate fumarate of claim 1, characterized by an X-Ray Powder Diffraction (XRPD) pattern exhibiting all of said peaks.

5. The crystalline form of nortriptyline-4-aminobutyrate fumarate of claim 1, characterized by an infrared spectrum exhibiting at least five of said absorption peaks.

6. The crystalline form of a fumaric acid addition salt of nortriptyline-4-aminobutyrate of claim 1, characterized by an infrared spectrum exhibiting all of said absorption peaks.

7. A crystalline form of nortriptyline-4-aminobutyrate fumarate, characterized by an X-Ray Powder Diffraction (XRPD) pattern exhibiting at least four peaks selected from the group of peaks having a refraction angle (2θ) of 3.8; 7.4; 10.2; 12.2; 13.0; 14.5; 15.2; 16.7; 18.6; 18.8; 19.2; 20.0; 20.6; 21.0; 21.7; 22.0; 23.0; 24.5; 24.8; 25.3; 26.1; 27.5; 31.0; and 37.5 degrees.

8. The crystalline form of nortriptyline-4-aminobutyrate fumarate of claim 7, characterized by an X-Ray Powder Diffraction (XRPD) pattern exhibiting at least six of said peaks.

9. The crystalline form of nortriptyline-4-aminobutyrate fumarate of claim 7, characterized by an X-Ray Powder Diffraction (XRPD) pattern exhibiting all of said peaks.

10. A crystalline form of nortriptyline-4-aminobutyrate fumarate characterized by a Differential Scanning Calorimetry (DSC) exhibiting an endothermic peak maximum that ranges from 155° C. to 160° C.

11. The crystalline form of fumaric acid addition salt of nortriptyline-4-aminobutyrate of claim 1, being obtainable by:
    (i) reacting a nortriptyline-4-aminobutyrate with fumaric acid, to thereby obtain the fumaric acid addition salt of nortriptyline-4-aminobutyrate; and
    (ii) contacting the fumaric acid addition salt of nortriptyline-4-aminobutyrate with diethyl ether.

12. A pharmaceutical composition comprising the crystalline form of nortriptyline-4-aminobutyrate fumarate salt of claim 1 and a pharmaceutically acceptable carrier.

13. The pharmaceutical composition of claim 12, being packaged in a packaging material and identified in print, in or on said packaging material, for use in the treatment of pain.

14. A process of preparing the crystalline form of fumaric acid addition salt of nortriptyline-4-aminobutyrate of claim 1, the process comprising:
    (i) reacting a nortriptyline-4-aminobutyrate with fumaric acid, to thereby obtain the fumaric acid addition salt of nortriptyline-4-aminobutyrate; and
    (ii) contacting the fumaric acid addition salt of nortriptyline-4-aminobutyrate with diethyl ether, thereby obtaining the crystalline form.

15. The process of claim 14, wherein said contacting comprises suspending the fumaric acid addition salt of nortriptyline-4-aminobutyrate in diethyl ether.

16. The process of claim 14, further comprising re-crystallizing the fumaric acid addition salt of nortriptyline-4-aminobutyrate from a solvent mixture that comprises ethanol, water and diethyl ether.

17. The process of claim 14, wherein said nortriptyline-4-aminobutyrate is prepared by reacting nortriptyline and N-protected 4-aminobutyric acid, to thereby obtain N-protected nortriptyline-4-aminobutyrate; and removing the N-protecting group.

18. The process of claim 17, wherein reacting nortriptyline and N-protected 4-aminobutyrate is performed in the presence of a coupling reagent.

19. The process of claim 18, wherein said coupling reagent comprises HOBt (1-Hydroxybenzotriazole).

20. The process of claim 19, wherein said coupling reagent further comprises EDAC (1-Ethyl-3-(3-dimethylaminopropyl)carbodiimide).

21. The process of claim 14, further comprising milling said crystalline form of fumarate acid addition salt of nortriptyline-4-aminobutyrate.

22. The process of claim 21, wherein said milling results in an average particle size of said crystalline form of fumarate acid addition salt of nortriptyline-4-aminobutyrate that is smaller than 100 microns.

23. A method of treating pain, the method comprising administering to a subject in need thereof a therapeutically effective amount of the crystalline form of the nortriptyline-4-aminobutyrate fumarate salt of claim 1, thereby treating pain.

* * * * *